(12) United States Patent
Tuval et al.

(10) Patent No.: US 8,137,398 B2
(45) Date of Patent: Mar. 20, 2012

(54) PROSTHETIC VALVE HAVING TAPERED TIP WHEN COMPRESSED FOR DELIVERY

(75) Inventors: Yosi Tuval, Netanya (IL); Igor Kovalsky, Givatayim (IL)

(73) Assignee: Medtronic Ventor Technologies Ltd, Netanya (IL)

( * ) Notice: Subject to any disclaimer, the term of this patent is extended or adjusted under 35 U.S.C. 154(b) by 17 days.

(21) Appl. No.: 12/250,163

(22) Filed: Oct. 13, 2008

(65) Prior Publication Data

US 2010/0094411 A1   Apr. 15, 2010

(51) Int. Cl.
*A61F 2/24* (2006.01)
(52) U.S. Cl. .............. 623/2.17; 623/2.1; 623/2.12
(58) Field of Classification Search ............ 623/1.15, 623/1.24, 1.3, 1.31, 2.1, 2.12, 2.17
See application file for complete search history.

(56) References Cited

U.S. PATENT DOCUMENTS

| | | | |
|---|---|---|---|
| 3,657,744 A | 4/1972 | Ersek |
| 3,671,979 A | 6/1972 | Moulopoulos |
| 3,714,671 A | 2/1973 | Edwards et al. |
| 3,755,823 A | 9/1973 | Hancock |
| 4,056,854 A | 11/1977 | Boretos et al. |
| 4,106,129 A | 8/1978 | Carpentier et al. |
| 4,222,126 A | 9/1980 | Boretos et al. |
| 4,265,694 A | 5/1981 | Boretos |
| 4,291,420 A | 9/1981 | Reul |
| 4,297,749 A | 11/1981 | Davis et al. |
| 4,339,831 A | 7/1982 | Johnson |
| 4,345,340 A | 8/1982 | Rosen |
| 4,425,908 A | 1/1984 | Simon |
| 4,470,157 A | 9/1984 | Love |
| 4,501,030 A | 2/1985 | Lane |
| 4,574,803 A | 3/1986 | Storz |
| 4,580,568 A | 4/1986 | Gianturco |
| 4,592,340 A | 6/1986 | Boyles |
| 4,610,688 A | 9/1986 | Silvestrini et al. |
| 4,612,011 A | 9/1986 | Kautzky |
| 4,655,771 A | 4/1987 | Wallsten |
| 4,662,885 A | 5/1987 | DiPisa, Jr. |
| 4,665,906 A | 5/1987 | Jervis |

(Continued)

FOREIGN PATENT DOCUMENTS

CN   2007-100074433   8/2007

(Continued)

OTHER PUBLICATIONS

Andersen, H.R. et al, "Transluminal implantation of artificial heart valves. Description of a new expandable aortic valve and initial results with implantation by catheter technique in closed chest pigs." Euro. Heart J. (1992) 13:704-708.

(Continued)

*Primary Examiner* — Thomas J Sweet
*Assistant Examiner* — Seema Swaminathan

(57) ABSTRACT

Apparatus is provided that includes a valve prosthesis for attachment to a native valve complex of a subject. The prosthesis is configured to assume a compressed delivery state and an uncompressed implantation state. The prosthesis includes a support frame, which is shaped so as to define an upstream inlet having upstream-most portions that are tapered in an upstream direction toward a central longitudinal axis of the prosthesis when the prosthesis assumes the compressed delivery state. The prosthesis further includes a flexible prosthetic heart valve component, coupled to the support frame. Other embodiments are also described.

16 Claims, 7 Drawing Sheets

U.S. PATENT DOCUMENTS

| | | |
|---|---|---|
| 4,681,908 A | 7/1987 | Broderick et al. |
| 4,710,192 A | 12/1987 | Liotta et al. |
| 4,777,951 A | 10/1988 | Cribier et al. |
| 4,787,899 A | 11/1988 | Lazarus |
| 4,796,629 A | 1/1989 | Grayzel |
| 4,797,901 A | 1/1989 | Goerne et al. |
| 4,819,751 A | 4/1989 | Shimada et al. |
| 4,834,755 A | 5/1989 | Silvestrini et al. |
| 4,856,516 A | 8/1989 | Hillstead |
| 4,872,874 A | 10/1989 | Taheri |
| 4,878,495 A | 11/1989 | Grayzel |
| 4,878,906 A | 11/1989 | Lindemann et al. |
| 4,883,458 A | 11/1989 | Shiber |
| 4,909,252 A | 3/1990 | Goldberger |
| 4,917,102 A | 4/1990 | Miller et al. |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,047,041 A | 9/1991 | Samuels |
| 5,059,177 A | 10/1991 | Towne et al. |
| 5,085,635 A | 2/1992 | Cragg |
| 5,089,015 A | 2/1992 | Ross |
| 5,152,771 A | 10/1992 | Sabbaghian et al. |
| 5,163,953 A | 11/1992 | Vince |
| 5,167,628 A | 12/1992 | Boyles |
| 5,232,445 A | 8/1993 | Bonzel |
| 5,272,909 A | 12/1993 | Nguyen et al. |
| 5,295,958 A | 3/1994 | Shturman |
| 5,327,774 A | 7/1994 | Nguyen et al. |
| 5,332,402 A | 7/1994 | Teitelbaum |
| 5,350,398 A | 9/1994 | Pavcnik et al. |
| 5,370,685 A | 12/1994 | Stevens |
| 5,397,351 A | 3/1995 | Pavcnik et al. |
| 5,411,552 A | 5/1995 | Andersen et al. |
| 5,415,633 A | 5/1995 | Lazarus et al. |
| 5,431,676 A | 7/1995 | Dubrul et al. |
| 5,443,446 A | 8/1995 | Shturman |
| 5,449,384 A | 9/1995 | Johnson |
| 5,480,424 A | 1/1996 | Cox |
| 5,489,294 A | 2/1996 | McVenes et al. |
| 5,489,297 A | 2/1996 | Duran |
| 5,496,346 A | 3/1996 | Horzewski et al. |
| 5,500,014 A | 3/1996 | Quijano et al. |
| 5,507,767 A | 4/1996 | Maeda et al. |
| 5,545,209 A | 8/1996 | Roberts et al. |
| 5,545,211 A | 8/1996 | An et al. |
| 5,545,214 A | 8/1996 | Stevens |
| 5,554,185 A | 9/1996 | Block et al. |
| 5,575,818 A | 11/1996 | Pinchuk |
| 5,580,922 A | 12/1996 | Park et al. |
| 5,591,195 A | 1/1997 | Taheri et al. |
| 5,609,626 A | 3/1997 | Quijano et al. |
| 5,645,559 A | 7/1997 | Hachtman et al. |
| 5,665,115 A | 9/1997 | Cragg |
| 5,667,523 A | 9/1997 | Bynon et al. |
| 5,674,277 A | 10/1997 | Freitag |
| 5,695,498 A | 12/1997 | Tower |
| 5,702,368 A | 12/1997 | Stevens et al. |
| 5,713,953 A | 2/1998 | Vallana et al. |
| 5,716,417 A | 2/1998 | Girard et al. |
| 5,746,709 A | 5/1998 | Rom et al. |
| 5,749,890 A | 5/1998 | Shaknovich |
| 5,766,151 A | 6/1998 | Valley et al. |
| 5,782,809 A | 7/1998 | Umeno et al. |
| 5,800,456 A | 9/1998 | Maeda et al. |
| 5,800,508 A | 9/1998 | Goicoechea et al. |
| 5,817,126 A | 10/1998 | Imran |
| 5,824,041 A | 10/1998 | Lenker et al. |
| 5,824,043 A | 10/1998 | Cottone, Jr. |
| 5,824,053 A | 10/1998 | Khosravi et al. |
| 5,824,056 A | 10/1998 | Rosenberg |
| 5,824,061 A | 10/1998 | Quijano et al. |
| 5,824,064 A | 10/1998 | Taheri |
| 5,843,158 A | 12/1998 | Lenker et al. |
| 5,851,232 A | 12/1998 | Lois |
| 5,855,597 A | 1/1999 | Jayaraman |
| 5,855,601 A | 1/1999 | Bessler et al. |
| 5,861,028 A | 1/1999 | Angell |
| 5,888,201 A | 3/1999 | Stinson et al. |
| 5,891,191 A | 4/1999 | Stinson |
| 5,906,619 A | 5/1999 | Olson et al. |
| 5,913,842 A | 6/1999 | Boyd et al. |
| 5,925,063 A | 7/1999 | Khosravi |
| 5,944,738 A | 8/1999 | Amplatz et al. |
| 5,957,949 A | 9/1999 | Leonhardt et al. |
| 5,968,068 A | 10/1999 | Dehdashtian et al. |
| 5,984,957 A | 11/1999 | Laptewicz, Jr. et al. |
| 5,997,573 A | 12/1999 | Quijano et al. |
| 6,027,525 A | 2/2000 | Suh et al. |
| 6,029,671 A | 2/2000 | Stevens et al. |
| 6,042,589 A | 3/2000 | Marianne |
| 6,042,598 A | 3/2000 | Tsugita et al. |
| 6,042,607 A | 3/2000 | Williamson, IV et al. |
| 6,051,104 A | 4/2000 | Oriaran et al. |
| 6,059,809 A | 5/2000 | Amor et al. |
| 6,110,201 A | 8/2000 | Quijano et al. |
| 6,146,366 A | 11/2000 | Schachar |
| 6,159,239 A | 12/2000 | Greenhalgh |
| 6,162,208 A | 12/2000 | Hipps |
| 6,162,245 A | 12/2000 | Jayaraman |
| 6,168,614 B1 | 1/2001 | Andersen et al. |
| 6,171,335 B1 | 1/2001 | Wheatley et al. |
| 6,200,336 B1 | 3/2001 | Pavcnik et al. |
| 6,203,550 B1 | 3/2001 | Olson |
| 6,210,408 B1 | 4/2001 | Chandrasekaran et al. |
| 6,218,662 B1 | 4/2001 | Tchakarov et al. |
| 6,221,006 B1 | 4/2001 | Dubrul et al. |
| 6,221,091 B1 | 4/2001 | Khosravi |
| 6,241,757 B1 | 6/2001 | An et al. |
| 6,245,102 B1 | 6/2001 | Jayaraman |
| 6,248,116 B1 | 6/2001 | Chevillion et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,277,555 B1 | 8/2001 | Duran et al. |
| 6,299,637 B1 | 10/2001 | Shaolian et al. |
| 6,302,906 B1 | 10/2001 | Goicoechea et al. |
| 6,309,382 B1 | 10/2001 | Garrison et al. |
| 6,309,417 B1 | 10/2001 | Spence et al. |
| 6,338,735 B1 | 1/2002 | Stevens |
| 6,348,063 B1 | 2/2002 | Yassour et al. |
| 6,350,277 B1 | 2/2002 | Kocur |
| 6,352,708 B1 | 3/2002 | Duran et al. |
| 6,371,970 B1 | 4/2002 | Khosravi et al. |
| 6,371,983 B1 | 4/2002 | Lane |
| 6,379,383 B1 | 4/2002 | Palmaz et al. |
| 6,380,457 B1 | 4/2002 | Yurek et al. |
| 6,398,807 B1 | 6/2002 | Chouinard et al. |
| 6,409,750 B1 | 6/2002 | Hyodoh et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,475,239 B1 | 11/2002 | Campbell et al. |
| 6,482,228 B1 | 11/2002 | Norred |
| 6,488,704 B1 | 12/2002 | Connelly et al. |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,562,031 B2 | 5/2003 | Chandrasekaran et al. |
| 6,562,058 B2 | 5/2003 | Seguin et al. |
| 6,569,196 B1 | 5/2003 | Vesely |
| 6,585,758 B1 | 7/2003 | Chouinard et al. |
| 6,592,546 B1 | 7/2003 | Barbut et al. |
| 6,605,112 B1 | 8/2003 | Moll et al. |
| 6,613,077 B2 | 9/2003 | Gilligan et al. |
| 6,622,604 B1 | 9/2003 | Chouinard et al. |

| Patent | Date | Inventor |
|---|---|---|
| 6,635,068 B1 | 10/2003 | Dubrul et al. |
| 6,652,571 B1 | 11/2003 | White et al. |
| 6,652,578 B2 | 11/2003 | Bailey et al. |
| 6,656,213 B2 | 12/2003 | Solem |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,698 B2 | 1/2004 | McGuckin, Jr. et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,695,878 B2 | 2/2004 | McGuckin, Jr. et al. |
| 6,702,851 B1 | 3/2004 | Chinn et al. |
| 6,719,789 B2 | 4/2004 | Cox |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton, III et al. |
| 6,769,434 B2 | 8/2004 | Liddicoat et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,792,979 B2 | 9/2004 | Konya et al. |
| 6,797,002 B2 | 9/2004 | Spence et al. |
| 6,821,297 B2 | 11/2004 | Snyders |
| 6,830,575 B2 | 12/2004 | Stenzel et al. |
| 6,830,584 B1 | 12/2004 | Seguin |
| 6,830,585 B1 | 12/2004 | Artof et al. |
| 6,846,325 B2 | 1/2005 | Liddicoat |
| 6,866,650 B2 | 3/2005 | Stevens et al. |
| 6,872,223 B2 | 3/2005 | Roberts et al. |
| 6,875,231 B2 | 4/2005 | Anduiza et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,893,460 B2 | 5/2005 | Spenser et al. |
| 6,896,690 B1 | 5/2005 | Lambrecht et al. |
| 6,908,481 B2 | 6/2005 | Cribier |
| 6,913,600 B2 | 7/2005 | Valley et al. |
| 6,929,653 B2 | 8/2005 | Strecter |
| 6,936,066 B2 | 8/2005 | Palmaz et al. |
| 6,939,365 B1 | 9/2005 | Fogarty et al. |
| 6,951,571 B1 | 10/2005 | Srivastava |
| 6,974,474 B2 | 12/2005 | Pavcnik et al. |
| 6,974,476 B2 | 12/2005 | McGuckin, Jr. et al. |
| 6,986,742 B2 | 1/2006 | Hart et al. |
| 6,989,027 B2 | 1/2006 | Allen et al. |
| 6,989,028 B2 | 1/2006 | Lashinski et al. |
| 6,991,649 B2 | 1/2006 | Sievers |
| 7,018,401 B1 | 3/2006 | Hyodoh et al. |
| 7,041,128 B2 | 5/2006 | McGuckin, Jr. et al. |
| 7,044,966 B2 | 5/2006 | Svanidze et al. |
| 7,048,014 B2 | 5/2006 | Hyodoh et al. |
| 7,097,659 B2 | 8/2006 | Woolfson et al. |
| 7,101,396 B2 | 9/2006 | Artof et al. |
| 7,105,016 B2 | 9/2006 | Shiu et al. |
| 7,115,141 B2 | 10/2006 | Menz et al. |
| 7,128,759 B2 | 10/2006 | Osborne et al. |
| 7,147,663 B1 | 12/2006 | Berg et al. |
| 7,153,324 B2 | 12/2006 | Case et al. |
| 7,160,319 B2 | 1/2007 | Chouinard et al. |
| 7,175,656 B2 | 2/2007 | Khairkhahan |
| 7,186,265 B2 | 3/2007 | Sharkawy et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,252,682 B2 | 8/2007 | Seguin |
| 7,300,457 B2 | 11/2007 | Palmaz |
| 7,300,463 B2 | 11/2007 | Liddicoat |
| 7,316,706 B2 | 1/2008 | Bloom et al. |
| 7,329,278 B2 | 2/2008 | Seguin et al. |
| 7,335,218 B2 | 2/2008 | Wilson et al. |
| 7,338,520 B2 | 3/2008 | Bailey et al. |
| 7,374,571 B2 | 5/2008 | Pease et al. |
| 7,377,938 B2 | 5/2008 | Sarac et al. |
| 7,381,218 B2 | 6/2008 | Schreck |
| 7,384,411 B1 | 6/2008 | Condado |
| 7,429,269 B2 * | 9/2008 | Schwammenthal et al. .. 623/2.14 |
| 7,442,204 B2 | 10/2008 | Schwammenthal et al. |
| 7,462,191 B2 | 12/2008 | Spenser et al. |
| 7,470,284 B2 | 12/2008 | Lambrecht et al. |
| 7,481,838 B2 | 1/2009 | Carpentier et al. |
| 7,544,206 B2 | 6/2009 | Cohn |
| 7,547,322 B2 | 6/2009 | Sarac et al. |
| 7,556,646 B2 | 7/2009 | Yang et al. |
| 7,806,919 B2 | 10/2010 | Bloom et al. |
| 2001/0001314 A1 | 5/2001 | Davison et al. |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0011189 A1 | 8/2001 | Drasler et al. |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0044647 A1 | 11/2001 | Pinchuk et al. |
| 2002/0010508 A1 | 1/2002 | Chobotov |
| 2002/0029014 A1 | 3/2002 | Jayaraman |
| 2002/0032480 A1 | 3/2002 | Spence et al. |
| 2002/0032481 A1 | 3/2002 | Gabbay |
| 2002/0035396 A1 | 3/2002 | Heath |
| 2002/0042650 A1 | 4/2002 | Vardi et al. |
| 2002/0052651 A1 | 5/2002 | Myers et al. |
| 2002/0058995 A1 | 5/2002 | Stevens |
| 2002/0072789 A1 | 6/2002 | Hackett et al. |
| 2002/0099439 A1 | 7/2002 | Schwartz et al. |
| 2002/0103533 A1 | 8/2002 | Langberg et al. |
| 2002/0107565 A1 | 8/2002 | Greenhalgh |
| 2002/0111674 A1 | 8/2002 | Chouinard et al. |
| 2002/0123802 A1 | 9/2002 | Snyders |
| 2002/0133183 A1 | 9/2002 | Lentz et al. |
| 2002/0138138 A1 | 9/2002 | Yang |
| 2002/0151970 A1 | 10/2002 | Garrison et al. |
| 2002/0161392 A1 | 10/2002 | Dubrul |
| 2002/0161394 A1 | 10/2002 | Macoviak et al. |
| 2002/0193871 A1 | 12/2002 | Beyersdorf et al. |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040771 A1 | 2/2003 | Hyodoh et al. |
| 2003/0040772 A1 | 2/2003 | Hyodoh et al. |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0069492 A1 | 4/2003 | Abrams et al. |
| 2003/0109924 A1 | 6/2003 | Cribier |
| 2003/0125795 A1 | 7/2003 | Pavcnik et al. |
| 2003/0130726 A1 | 7/2003 | Thorpe et al. |
| 2003/0130729 A1 | 7/2003 | Paniagua et al. |
| 2003/0139804 A1 | 7/2003 | Hankh et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0181850 A1 | 9/2003 | Diamond et al. |
| 2003/0191519 A1 | 10/2003 | Lombardi et al. |
| 2003/0199913 A1 | 10/2003 | Dubrul et al. |
| 2003/0199963 A1 | 10/2003 | Tower et al. |
| 2003/0199971 A1 | 10/2003 | Tower et al. |
| 2003/0212410 A1 | 11/2003 | Stenzel et al. |
| 2003/0212454 A1 | 11/2003 | Scott et al. |
| 2003/0225445 A1 | 12/2003 | Derus et al. |
| 2004/0019374 A1 | 1/2004 | Hojeibane et al. |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |

| | | | | | | |
|---|---|---|---|---|---|---|
| 2004/0049262 A1 | 3/2004 | Obermiller et al. | | 2005/0143807 A1 | 6/2005 | Pavcnik et al. |
| 2004/0049266 A1 | 3/2004 | Anduiza et al. | | 2005/0143809 A1 | 6/2005 | Salahieh et al. |
| 2004/0082904 A1 | 4/2004 | Houde et al. | | 2005/0148997 A1 | 7/2005 | Valley et al. |
| 2004/0088045 A1 | 5/2004 | Cox | | 2005/0149181 A1 | 7/2005 | Eberhardt |
| 2004/0092858 A1 | 5/2004 | Wilson et al. | | 2005/0165477 A1 | 7/2005 | Anduiza et al. |
| 2004/0092989 A1 | 5/2004 | Wilson et al. | | 2005/0187616 A1 | 8/2005 | Realyvasquez |
| 2004/0093005 A1 | 5/2004 | Durcan | | 2005/0197695 A1 | 9/2005 | Stacchino et al. |
| 2004/0093060 A1 | 5/2004 | Sequin et al. | | 2005/0203549 A1 | 9/2005 | Realyvasquez |
| 2004/0093075 A1 | 5/2004 | Kuehn | | 2005/0203605 A1 | 9/2005 | Dolan |
| 2004/0097788 A1 | 5/2004 | Mourles et al. | | 2005/0203618 A1 | 9/2005 | Sharkawy et al. |
| 2004/0098112 A1 | 5/2004 | DiMatteo et al. | | 2005/0222674 A1 | 10/2005 | Paine |
| 2004/0106976 A1 | 6/2004 | Bailey et al. | | 2005/0228495 A1 | 10/2005 | Macoviak |
| 2004/0106990 A1 | 6/2004 | Spence et al. | | 2005/0234546 A1 | 10/2005 | Nugent et al. |
| 2004/0111096 A1 | 6/2004 | Tu et al. | | 2005/0240200 A1 | 10/2005 | Bergheim |
| 2004/0116951 A1 | 6/2004 | Rosengart | | 2005/0240263 A1 | 10/2005 | Fogarty et al. |
| 2004/0117004 A1 | 6/2004 | Osborne et al. | | 2005/0261759 A1 | 11/2005 | Lambrecht et al. |
| 2004/0122468 A1 | 6/2004 | Yodfat et al. | | 2005/0283962 A1 | 12/2005 | Boudjemline |
| 2004/0122514 A1 | 6/2004 | Fogarty et al. | | 2006/0004439 A1 | 1/2006 | Spenser et al. |
| 2004/0122516 A1 | 6/2004 | Fogarty et al. | | 2006/0004469 A1 | 1/2006 | Sokel |
| 2004/0127979 A1 | 7/2004 | Wilson et al. | | 2006/0009841 A1 | 1/2006 | McGuckin, Jr. et al. |
| 2004/0138742 A1 | 7/2004 | Myers et al. | | 2006/0052867 A1 | 3/2006 | Revuelta et al. |
| 2004/0138743 A1 | 7/2004 | Myers et al. | | 2006/0058775 A1 | 3/2006 | Stevens et al. |
| 2004/0153146 A1 | 8/2004 | Lashinski et al. | | 2006/0089711 A1 | 4/2006 | Dolan |
| 2004/0167573 A1 | 8/2004 | Williamson, IV et al. | | 2006/0100685 A1 | 5/2006 | Seguin et al. |
| 2004/0167620 A1 | 8/2004 | Ortiz et al. | | 2006/0116757 A1 | 6/2006 | Lashinski et al. |
| 2004/0186563 A1 | 9/2004 | Iobbi | | 2006/0135964 A1 | 6/2006 | Vesely |
| 2004/0193261 A1 | 9/2004 | Berreklouw | | 2006/0142848 A1 | 6/2006 | Gabbay |
| 2004/0210240 A1 | 10/2004 | Saint | | 2006/0149360 A1* | 7/2006 | Schwammenthal et al. . 623/1.24 |
| 2004/0210304 A1 | 10/2004 | Seguin et al. | | 2006/0167474 A1 | 7/2006 | Bloom et al. |
| 2004/0210307 A1 | 10/2004 | Khairkhahan | | 2006/0178740 A1 | 8/2006 | Stacchino et al. |
| 2004/0215333 A1 | 10/2004 | Duran et al. | | 2006/0195134 A1 | 8/2006 | Crittenden |
| 2004/0215339 A1 | 10/2004 | Drasler et al. | | 2006/0206192 A1 | 9/2006 | Tower et al. |
| 2004/0225353 A1 | 11/2004 | McGuckin, Jr. et al. | | 2006/0206202 A1 | 9/2006 | Bonhoeffer et al. |
| 2004/0225354 A1 | 11/2004 | Allen et al. | | 2006/0212111 A1 | 9/2006 | Case et al. |
| 2004/0254636 A1 | 12/2004 | Flagle et al. | | 2006/0247763 A1 | 11/2006 | Slater |
| 2004/0260389 A1 | 12/2004 | Case et al. | | 2006/0259134 A1 | 11/2006 | Schwammenthal et al. |
| 2004/0260394 A1 | 12/2004 | Douk et al. | | 2006/0259136 A1 | 11/2006 | Nguyen et al. |
| 2004/0267357 A1 | 12/2004 | Allen et al. | | 2006/0259137 A1 | 11/2006 | Artof et al. |
| 2005/0010246 A1 | 1/2005 | Streeter et al. | | 2006/0265056 A1 | 11/2006 | Nguyen et al. |
| 2005/0010285 A1 | 1/2005 | Lambrecht et al. | | 2006/0271166 A1 | 11/2006 | Thill et al. |
| 2005/0010287 A1 | 1/2005 | Macoviak et al. | | 2006/0271175 A1 | 11/2006 | Woolfson et al. |
| 2005/0015112 A1 | 1/2005 | Cohn et al. | | 2006/0276874 A1 | 12/2006 | Wilson et al. |
| 2005/0027348 A1 | 2/2005 | Case et al. | | 2006/0276882 A1 | 12/2006 | Case et al. |
| 2005/0033398 A1 | 2/2005 | Seguin | | 2006/0282161 A1 | 12/2006 | Huynh et al. |
| 2005/0043790 A1 | 2/2005 | Seguin | | 2007/0005129 A1 | 1/2007 | Damm et al. |
| 2005/0049692 A1 | 3/2005 | Numamoto et al. | | 2007/0005131 A1 | 1/2007 | Taylor |
| 2005/0049696 A1 | 3/2005 | Siess et al. | | 2007/0010878 A1 | 1/2007 | Raffiee et al. |
| 2005/0055088 A1 | 3/2005 | Liddicoat et al. | | 2007/0016286 A1 | 1/2007 | Herrmann et al. |
| 2005/0060029 A1 | 3/2005 | Le et al. | | 2007/0027518 A1 | 2/2007 | Case et al. |
| 2005/0060030 A1 | 3/2005 | Lashinski et al. | | 2007/0027533 A1 | 2/2007 | Douk |
| 2005/0075584 A1 | 4/2005 | Cali | | 2007/0038295 A1 | 2/2007 | Case et al. |
| 2005/0075712 A1 | 4/2005 | Biancucci et al. | | 2007/0043431 A1 | 2/2007 | Melsheimer |
| 2005/0075717 A1 | 4/2005 | Nguyen et al. | | 2007/0043435 A1 | 2/2007 | Seguin et al. |
| 2005/0075719 A1 | 4/2005 | Bergheim | | 2007/0051377 A1 | 3/2007 | Douk et al. |
| 2005/0075724 A1 | 4/2005 | Svanidze et al. | | 2007/0073392 A1 | 3/2007 | Heyninck-Janitz et al. |
| 2005/0075727 A1 | 4/2005 | Wheatley | | 2007/0078509 A1 | 4/2007 | Lotfy et al. |
| 2005/0075730 A1 | 4/2005 | Myers et al. | | 2007/0078510 A1 | 4/2007 | Ryan |
| 2005/0075731 A1 | 4/2005 | Artof et al. | | 2007/0088431 A1 | 4/2007 | Bourang et al. |
| 2005/0085841 A1 | 4/2005 | Eversull et al. | | 2007/0093869 A1 | 4/2007 | Bloom et al. |
| 2005/0085842 A1 | 4/2005 | Eversull et al. | | 2007/0100439 A1 | 5/2007 | Cangialosi et al. |
| 2005/0085843 A1 | 4/2005 | Opolski et al. | | 2007/0100440 A1 | 5/2007 | Figulla et al. |
| 2005/0085890 A1 | 4/2005 | Rasmussen et al. | | 2007/0100449 A1 | 5/2007 | O'Neil et al. |
| 2005/0085900 A1 | 4/2005 | Case et al. | | 2007/0112415 A1 | 5/2007 | Bartlett |
| 2005/0096568 A1 | 5/2005 | Kato | | 2007/0162102 A1 | 7/2007 | Ryan et al. |
| 2005/0096692 A1 | 5/2005 | Linder et al. | | 2007/0162113 A1 | 7/2007 | Sharkawy et al. |
| 2005/0096724 A1 | 5/2005 | Stenzel et al. | | 2007/0185513 A1 | 8/2007 | Woolfson et al. |
| 2005/0096734 A1 | 5/2005 | Majercak et al. | | 2007/0203391 A1 | 8/2007 | Bloom et al. |
| 2005/0096735 A1 | 5/2005 | Hojeibane et al. | | 2007/0225681 A1 | 9/2007 | House |
| 2005/0096736 A1 | 5/2005 | Osse et al. | | 2007/0232898 A1 | 10/2007 | Huynh et al. |
| 2005/0096738 A1 | 5/2005 | Cali et al. | | 2007/0233228 A1 | 10/2007 | Eberhardt et al. |
| 2005/0107871 A1 | 5/2005 | Realyvasquez et al. | | 2007/0233237 A1 | 10/2007 | Krivoruchko |
| 2005/0113910 A1 | 5/2005 | Paniagua et al. | | 2007/0233238 A1 | 10/2007 | Huynh et al. |
| 2005/0119688 A1 | 6/2005 | Berheim | | 2007/0238979 A1 | 10/2007 | Huynh et al. |
| 2005/0131438 A1 | 6/2005 | Cohn | | 2007/0239254 A1 | 10/2007 | Chia et al. |
| 2005/0137686 A1 | 6/2005 | Salahieh et al. | | 2007/0239265 A1 | 10/2007 | Birdsall |
| 2005/0137688 A1 | 6/2005 | Salahieh et al. | | 2007/0239266 A1 | 10/2007 | Birdsall |
| 2005/0137692 A1 | 6/2005 | Haug et al. | | 2007/0239269 A1 | 10/2007 | Dolan et al. |
| 2005/0137695 A1 | 6/2005 | Salahieh et al. | | 2007/0239273 A1 | 10/2007 | Allen |
| 2005/0137701 A1 | 6/2005 | Salahieh et al. | | 2007/0244544 A1 | 10/2007 | Birdsall et al. |

| | | |
|---|---|---|
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255394 A1 | 11/2007 | Ryan |
| 2007/0255396 A1 | 11/2007 | Douk et al. |
| 2007/0288000 A1 | 12/2007 | Bonan |
| 2008/0004696 A1 | 1/2008 | Vesely |
| 2008/0009940 A1 | 1/2008 | Cribier |
| 2008/0015671 A1 | 1/2008 | Bonhoeffer |
| 2008/0021552 A1 | 1/2008 | Gabbay |
| 2008/0048656 A1 | 2/2008 | Tan et al. |
| 2008/0065001 A1 | 3/2008 | DiNucci et al. |
| 2008/0065206 A1 | 3/2008 | Liddicoat |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0077234 A1 | 3/2008 | Styrc |
| 2008/0082165 A1 | 4/2008 | Wilson et al. |
| 2008/0082166 A1 | 4/2008 | Styrc et al. |
| 2008/0133003 A1 | 6/2008 | Seguin et al. |
| 2008/0140189 A1 | 6/2008 | Nguyen et al. |
| 2008/0147105 A1 | 6/2008 | Wilson et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0154355 A1 | 6/2008 | Benichou et al. |
| 2008/0154356 A1 | 6/2008 | Obermiller et al. |
| 2008/0161910 A1 | 7/2008 | Revuelta et al. |
| 2008/0161911 A1 | 7/2008 | Revuelta et al. |
| 2008/0172119 A1* | 7/2008 | Yamasaki et al. ............ 623/1.11 |
| 2008/0183273 A1 | 7/2008 | Mesana et al. |
| 2008/0188928 A1 | 8/2008 | Salahieh et al. |
| 2008/0215143 A1 | 9/2008 | Seguin |
| 2008/0215144 A1 | 9/2008 | Ryan et al. |
| 2008/0228254 A1 | 9/2008 | Ryan |
| 2008/0228263 A1 | 9/2008 | Ryan |
| 2008/0234797 A1 | 9/2008 | Styrc |
| 2008/0243246 A1 | 10/2008 | Ryan et al. |
| 2008/0255651 A1 | 10/2008 | Dwork |
| 2008/0255660 A1 | 10/2008 | Guyenot et al. |
| 2008/0255661 A1 | 10/2008 | Straubinger et al. |
| 2008/0262593 A1 | 10/2008 | Ryan et al. |
| 2008/0269878 A1 | 10/2008 | Iobbi |
| 2009/0005863 A1 | 1/2009 | Goetz et al. |
| 2009/0012600 A1 | 1/2009 | Styrc et al. |
| 2009/0048656 A1 | 2/2009 | Wen |
| 2009/0054976 A1 | 2/2009 | Tuval et al. |
| 2009/0069886 A1 | 3/2009 | Suri et al. |
| 2009/0069887 A1 | 3/2009 | Righini et al. |
| 2009/0069889 A1 | 3/2009 | Suri et al. |
| 2009/0082858 A1 | 3/2009 | Nugent et al. |
| 2009/0085900 A1 | 4/2009 | Weiner |
| 2009/0099653 A1 | 4/2009 | Suri et al. |
| 2009/0138079 A1 | 5/2009 | Tuval et al. |
| 2009/0164004 A1 | 6/2009 | Cohn |
| 2009/0171447 A1 | 7/2009 | VonSeggesser et al. |
| 2009/0192585 A1 | 7/2009 | Bloom et al. |
| 2009/0192586 A1 | 7/2009 | Tabor et al. |
| 2009/0192591 A1 | 7/2009 | Ryan et al. |
| 2009/0198316 A1 | 8/2009 | Laske et al. |
| 2009/0216310 A1 | 8/2009 | Straubinger et al. |
| 2009/0216312 A1 | 8/2009 | Straubinger et al. |
| 2009/0216313 A1 | 8/2009 | Straubinger et al. |
| 2009/0222082 A1 | 9/2009 | Lock et al. |
| 2009/0234443 A1 | 9/2009 | Ottma et al. |
| 2009/0240264 A1 | 9/2009 | Tuval et al. |
| 2009/0240320 A1 | 9/2009 | Tuval et al. |
| 2009/0287296 A1 | 11/2009 | Manasse |
| 2010/0036479 A1 | 2/2010 | Hill et al. |
| 2010/0094411 A1 | 4/2010 | Tuval et al. |
| 2010/0100167 A1 | 4/2010 | Bortlein et al. |
| 2010/0131054 A1 | 5/2010 | Tuval et al. |
| 2010/0137979 A1 | 6/2010 | Tuval et al. |
| 2010/0161045 A1 | 6/2010 | Righini |
| 2010/0198346 A1 | 8/2010 | Keogh et al. |
| 2010/0234940 A1 | 9/2010 | Dolan |
| 2010/0256723 A1 | 10/2010 | Murray |
| 2010/0268332 A1* | 10/2010 | Tuval et al. ............ 623/2.1 |
| 2011/0098804 A1* | 4/2011 | Yeung et al. ............ 623/2.1 |
| 2011/0172765 A1* | 7/2011 | Nguyen et al. ............ 623/2.18 |

FOREIGN PATENT DOCUMENTS

| | | |
|---|---|---|
| DE | 3640745 | 6/1987 |
| DE | 195 32 846 | 3/1997 |
| DE | 195 46 692 A1 | 6/1997 |
| DE | 195 46 692 C2 | 6/1997 |
| DE | 198 57 887 A1 | 7/2000 |
| DE | 199 07 646 | 8/2000 |
| DE | 100 49 812 | 4/2002 |
| DE | 100 49 813 | 4/2002 |
| DE | 100 49 815 | 4/2002 |
| EP | 1057460 A1 | 6/2000 |
| EP | 1255510 | 11/2002 |
| EP | 1469797 | 11/2005 |
| FR | 2788217 | 12/1999 |
| FR | 2815844 | 5/2000 |
| GB | 2056023 | 3/1981 |
| GB | 2433700 | 12/2007 |
| SU | 1271508 | 11/1986 |
| WO | 95/29640 | 11/1995 |
| WO | 00/47136 | 8/2000 |
| WO | 01/35870 | 5/2001 |
| WO | 01/49213 | 7/2001 |
| WO | 01/54625 | 8/2001 |
| WO | 01/62189 | 8/2001 |
| WO | 01/64137 | 9/2001 |
| WO | 02/22054 | 3/2002 |
| WO | 02/36048 | 5/2002 |
| WO | 03/003943 | 1/2003 |
| WO | 03/003949 | 1/2003 |
| WO | 03/011195 | 2/2003 |
| WO | 2004/019825 | 3/2004 |
| WO | 2004/089250 | 10/2004 |
| WO | 2005/004753 | 1/2005 |
| WO | 2005/046528 | 5/2005 |
| WO | 2006/026371 | 3/2006 |
| WO | 2008/047354 | 4/2008 |
| WO | 2008/138584 | 11/2008 |
| WO | 2008/150529 | 12/2008 |
| WO | 2009/002548 | 12/2008 |
| WO | 2009/029199 | 3/2009 |
| WO | 2009/042196 | 4/2009 |
| WO | 2009/045338 | 4/2009 |
| WO | 2009/061389 | 5/2009 |
| WO | 2009/091509 | 7/2009 |
| WO | 2009/111241 | 9/2009 |

OTHER PUBLICATIONS

Babaliaros, et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007; 107:87-96.

Bailey, "Percutaneous Expandable Prosthetic Valves," In: Topol EJ, ed. Textbook of Interventional Cardiology. vol. II. Second edition. WB Saunders, Philadelphia, 1994:1268-1276.

Block, et al., "Percutaneous Approaches to Valvular Heart Disease," Current Cardiology Reports, vol. 7 (2005) pp. 108-113.

Bonhoeffer, et al, "Percutaneous Insertion of the Pulmonary Valve," Journal of the American College of Cardiology (United States), May 15, 2002, pp. 1664-1669.

Bonhoeffer, et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-1405.

Bonhoeffer, et al, "Transcatheter Implantation of a Bovine Valve in Pulmonary Position: A Lamb Study," Circulation (United States), Aug. 15, 2000, pp. 813-816.

Boudjemline, et al, "Images in Cardiovascular Medicine. Percutaneous Aortic Valve Replacement in Animals," Circulation (United States), Mar. 16, 2004, 109, p. e161.

Boudjemline, et al, "Is Percutaneous Implantation of a Bovine Venous Valve in the Inferior Vena Cava a Reliable Technique to Treat Chronic Venous Insufficiency Syndrome?" Medical Science Monitor—International Medical Journal of Experimental and Clinical Research (Poland), Mar. 2004, pp. BR61-BR66.

Boudjemline, et al, "Off-pump Replacement of the Pulmonary Valve in Large Right Ventricular Outflow Tracts: A Hybrid Approach," Journal of Thoracic and Cardiovascular Surgery (United States), Apr. 2005, pp. 831-837.

Boudjemline, et al, "Percutaneous Aortic Valve Replacement: Will We Get There?" Heart (British Cardiac Society) (England), Dec. 2001, pp. 705-706.

Boudjemline, et al, "Percutaneous Implantation of a Biological Valve in the Aorta to Treat Aortic Valve Insufficiency—A Sheep Study," Medical Science Monitor—International Medical Journal of Experimental and Clinical Research (Poland), Apr. 2002, pp. BR113-BR116.

Boudjemline, et al, "Percutaneous Implantation of a Biological Valve in Aortic Position: Preliminary Results in a Sheep Study," European Heart Journal 22, Sep. 2001, p. 630.

Boudjemline, et al, "Percutaneous Implantation of a Valve in the Descending Aorta in Lambs," European Heart Journal (England), Jul. 2002, pp. 1045-1049.

Boudjemline, et al, "Percutaneous Pulmonary Valve Replacement in a Large Right Ventricular Outflow Tract: An Experimental Study," Journal of the American College of Cardiology (United States), Mar. 17, 2004, pp. 1082-1087.

Boudjemline, et al, "Percutaneous Valve Insertion: A New Approach," Journal of Thoracic and Cardiovascular Surgery (United States), Mar. 2003, pp. 741-742.

Boudjemline, et al, "Stent Implantation Combined with a Valve Replacement to Treat Degenerated Right Ventricle to Pulmonary Artery Prosthetic Conduits," European Heart Journal 22, Sep. 2001, p. 355.

Boudjemline, et al, "Steps Toward Percutaneous Aortic Valve Replacement," Circulation (United States), Feb. 12, 2002, pp. 775-778.

Boudjemline, et al, "The Percutaneous Implantable Heart Valve," Progress in Pediatric Cardiology (Ireland), 2001, pp. 89-93.

Boudjemline, et al, "Transcatheter Reconstruction of the Right Heart," Cardiology in the Young (England), Jun. 2003, pp. 308-311.

Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.

Cribier, A. et al, "Percutaneous Transcatheter Implantation of an Aortic Valve Prosthesis for Calcific Aortic Stenosis: First Human Case Description," Circulation (2002) 3006-3008.

Davidson et al., "Percutaneous therapies for valvular heart disease," Cardiovascular Pathology 15 (2006) 123-129.

Hanzel, et al., "Complications of percutaneous aortic valve replacement: experience with the Criber-Edwards™ percutaneous heart valve," EuroIntervention Supplements (2006), 1 (Supplement A) A3-A8.

Huber, et al., "Do Valved Stents Compromise Coronary Flow?" Eur. J. Cardiothorac. Surg. 2004;25:754-759.

Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.

Khambadkone, et al, "Percutaneous Implantation of Pulmonary Valves," Expert Review of Cardiovascular Therapy (England), Nov. 2003, pp. 541-548.

Khambadkone, et al, "Percutaneous Pulmonary Valve Implantation: Early and Medium Term Results," Circulation 108 (17 Supplement), Oct. 28, 2003, p. IV-375.

Khambadkone, et al, "Percutaneous Pulmonary Valve Implantation: Impact of Morphology on Case Selection," Circulation 108 (17 Supplement), Oct. 28, 2003, pp. IV-642-IV-643.

Lutter, et al, "Percutaneous Aortic Valve Replacement: An Experimental Study. I. Studies on Implantation," The Journal of Thoracic and Cardiovascular Surgery, Apr. 2002, pp. 768-776.

Lutter, et al, "Percutaneous Valve Replacement: Current State and Future Prospects," Annals of Thoracic Surgery (Netherlands), Dec. 2004, pp. 2199-2206.

Ma, Ling, et al., "Double-crowned valved stents for off-pump mitral valve replacement," European Journal of Cardio Thoracic Surgery, 28:194-198, 2005.

Medtech Insight, "New Frontiers in Heart Valve Disease," vol. 7, No. 8 (2005).

Palacios, "Percutaneous Valve Replacement and Repair, Fiction or Reality?" Journal of American College of Cardiology, vol. 44, No. 8 (2004) pp. 1662-1663.

Pelton et al., "Medical Uses of Nitinol," Materials Science Forum vols. 327-328, pp. 63-70 (2000).

Ruiz, "Transcathether Aortic Valve Implantation and Mitral Valve Repair: State of the Art," Pediatric Cardiology, vol. 26, No. 3 (2005).

Saliba, et al, "Treatment of Obstructions of Prosthetic Conduits by Percutaneous Implantation of Stents," Archives des Maldies du Coeur et des Vaisseaux (France), 1999, pp. 591-596.

Webb, et al., "Percutaneous Aortic Valve Implantation Retrograde from the Femoral Artery," Circulation (2006), 113;842-850.

Stassano et al., "Mid-term results of the valve-on-valve technique for bioprosthetic failure," Eur. J. Cardiothorac. Surg. 2000; 18:453-457.

Pavcnik et al., "Aortic and venous valve for percutaneous insertion," Min. Invas. Ther. & Allied Techol. 2000, vol. 9, pp. 287-292.

* cited by examiner

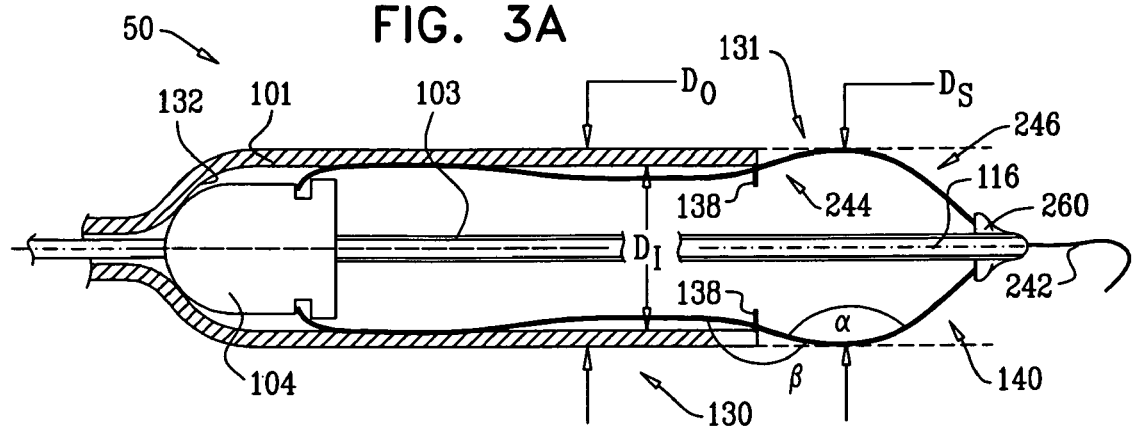
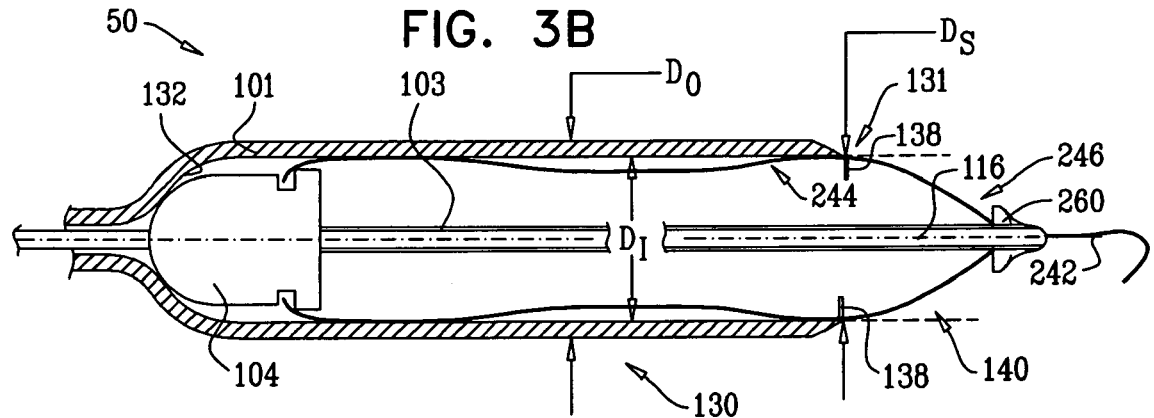
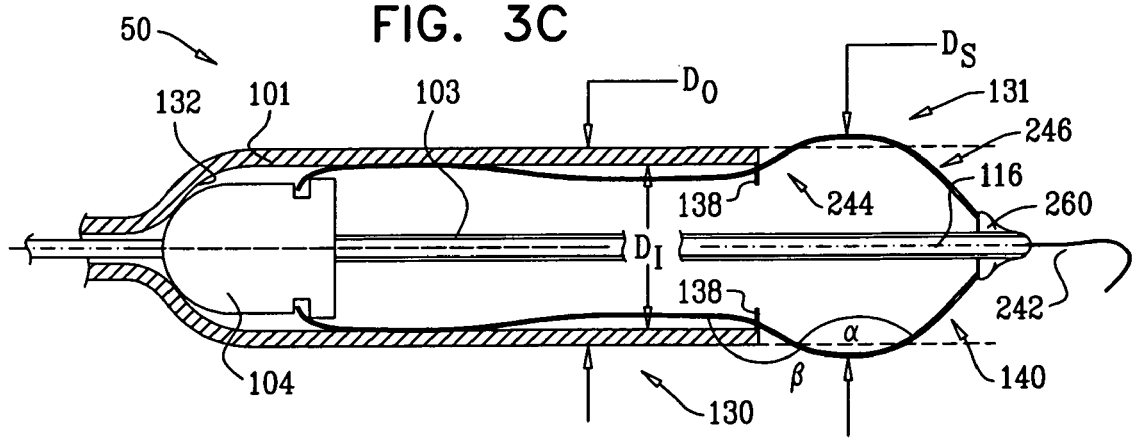

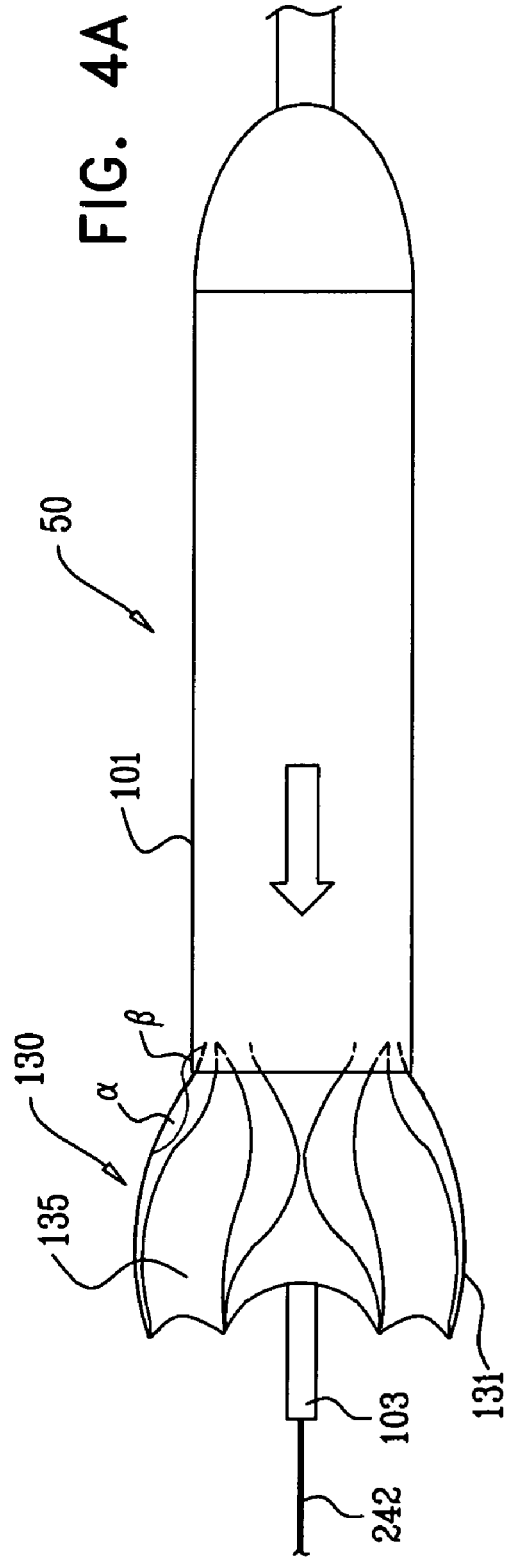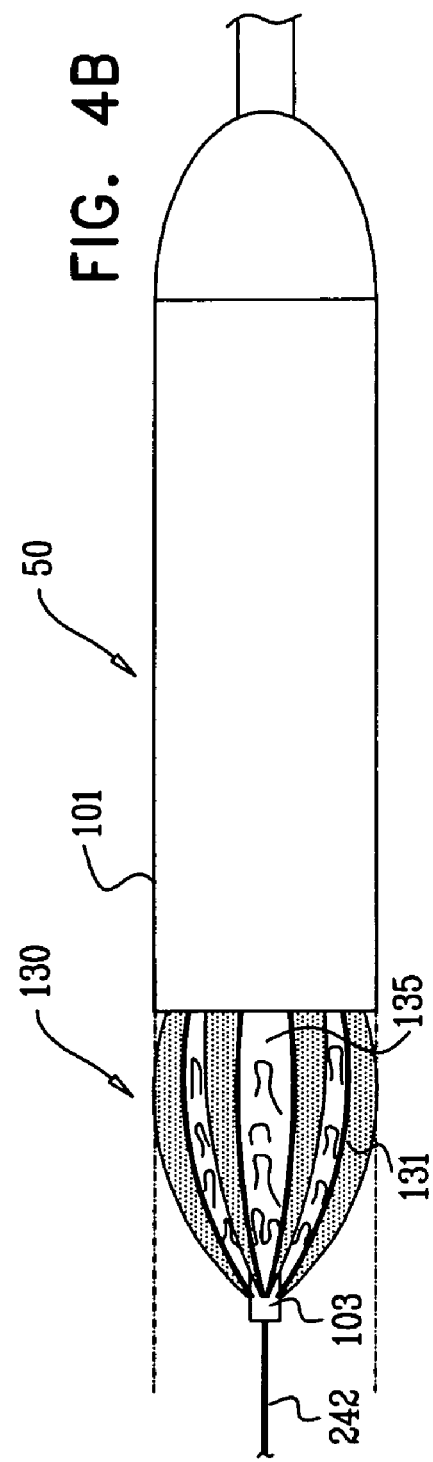

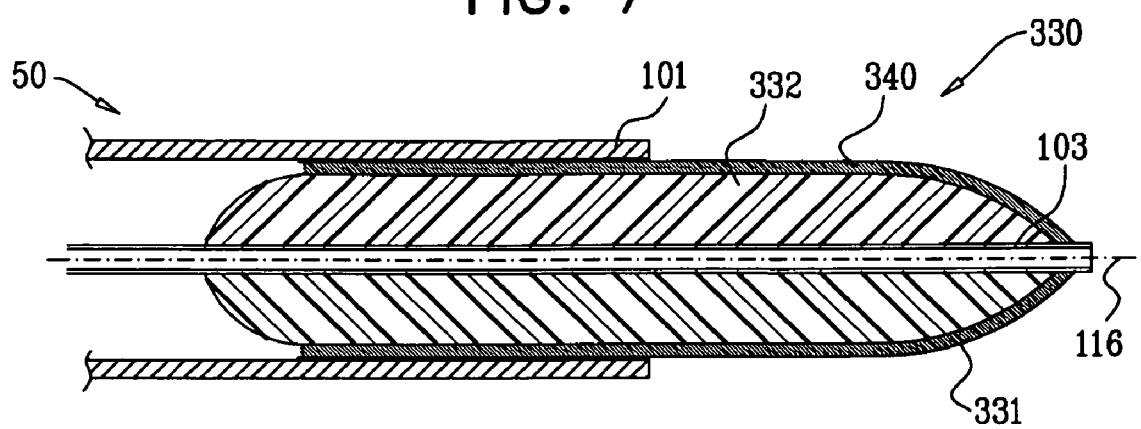

PROSTHETIC VALVE HAVING TAPERED TIP WHEN COMPRESSED FOR DELIVERY

FIELD OF THE INVENTION

The present invention relates generally to prosthetic heart valves, and specifically to prosthetic heart values configured for delivery using a catheter.

BACKGROUND OF THE INVENTION

Aortic valve replacement in patients with severe valve disease is a common surgical procedure. The replacement is conventionally performed by open heart surgery, in which the heart is usually arrested and the patient is placed on a heart bypass machine. In recent years, prosthetic heart valves have been developed which are implanted using minimally invasive procedures such as transapical or percutaneous approaches. These methods involve compressing the prosthesis radially to reduce its diameter, inserting the prosthesis into a delivery tool, such as a catheter, and advancing the delivery tool to the correct anatomical position in the heart. Once properly positioned, the prosthesis is deployed by radial expansion within the native valve annulus.

PCT Publication WO 05/002466 to Schwammenthal et al., relevant portions of which are incorporated herein by reference, describes prosthetic devices for treating aortic stenosis.

PCT Publication WO 06/070372 to Schwammenthal et al., relevant portions of which are incorporated herein by reference, describes a prosthetic device having a single flow field therethrough, adapted for implantation in a subject, and shaped so as to define a fluid inlet and a diverging section, distal to the fluid inlet.

US Patent Application Publication 2006/0149360 to Schwammenthal et al., relevant portions of which are incorporated herein by reference, describes a prosthetic device including a valve-orifice attachment member attachable to a valve in a blood vessel and including a fluid inlet, and a diverging member that extends from the fluid inlet, the diverging member including a proximal end near the fluid inlet and a distal end distanced from the proximal end. A distal portion of the diverging member has a larger cross-sectional area for fluid flow therethrough than a proximal portion thereof US Patent Application Publication 2004/0186563 to Iobbi describes a prosthetic heart valve having an internal support frame with a continuous, undulating leaflet frame defined therein. The leaflet frame has three cusp regions positioned at an inflow end intermediate three commissure regions positioned at an outflow end thereof The leaflet frame may be cloth covered and flexible leaflets attached thereto form occluding surfaces of the valve. The support frame further includes three cusp positioners rigidly fixed with respect to the leaflet frame and located at the outflow end of the support frame intermediate each pair of adjacent commissure regions. The valve is desirably compressible so as to be delivered in a minimally invasive manner through a catheter to the site of implantation. Upon expulsion from catheter, the valve expands into contact with the surrounding native valve annulus and is anchored in place without the use of sutures. In the aortic valve position, the cusp positioners angle outward into contact with the sinus cavities, and compress the native leaflets if they are not excised, or the aortic wall if they are. The support frame may be formed from a flat sheet of Nitinol that is bent into a three-dimensional configuration and heat set. A holder having spring-like arms connected to inflow projections of the valve may be used to deliver, reposition and re-collapse the valve, if necessary.

U.S. Pat. No. 7,018,408 to Bailey et al. describes prosthetic cardiac and venous valves and a single catheter device, and minimally invasive techniques for percutaneous and transluminal valvuloplasty and prosthetic valve implantation.

U.S. Pat. No. 6,730,118 to Spenser et al. describes a valve prosthesis device suitable for implantation in body ducts. The device comprises a support stent, comprised of a deployable construction adapted to be initially crimped in a narrow configuration suitable for catheterization through the body duct to a target location and adapted to be deployed by exerting substantially radial forces from within by means of a deployment device to a deployed state in the target location, and a valve assembly comprising a flexible conduit having an inlet end and an outlet, made of pliant material attached to the support beams providing collapsible slack portions of the conduit at the outlet. The support stent is provided with a plurality of longitudinally rigid support beams of fixed length. When flow is allowed to pass through the valve prosthesis device from the inlet to the outlet, the valve assembly is kept in an open position, whereas a reverse flow is prevented as the collapsible slack portions of the valve assembly collapse inwardly providing blockage to the reverse flow.

US Patent Application Publication 2006/0074485 to Realyvasquez describes methods and apparatus for valve repair or replacement. In one embodiment, the apparatus is a valve delivery device comprising a first apparatus and a second apparatus. The first apparatus includes a heart valve support having a proximal portion and a distal portion and a heart valve excisor slidably mounted on said first apparatus. The second apparatus includes a fastener assembly having a plurality of penetrating members mounted to extend outward when the assembly assumes an expanded configuration; and a heart valve prosthesis being releasably coupled to said second apparatus. The first apparatus and second apparatus are sized and configured for delivery to the heart through an opening formed in a femoral blood vessel. The heart valve prosthesis support is movable along a longitudinal axis of the device to engage tissue disposed between the anvil and the valve prosthesis. The system may include a tent and/or an embolic screen to capture debris from valve removal.

U.S. Pat. No. 7,018,408 to Bailey et al. describes prosthetic cardiac and venous valves and a single catheter device and minimally invasive techniques for percutaneous and transluminal valvuloplasty and prosthetic valve implantation.

The following patents and patent application publications, relevant portions of which are incorporated herein by reference, may be of interest:

US Patent Application Publication 2004/0039436 to Spenser et al.

US Patent Application Publication 2005/0197695 to Stacchino et al.

U.S. Pat. No. 6,312,465 to Griffin et al.

U.S. Pat. No. 5,908,451 to Yeo

U.S. Pat. No. 5,344,442 to Deac

U.S. Pat. No. 5,354,330 to Hanson

US Patent Application Publication 2004/0260389 to Case et al.

U.S. Pat. No. 6,730,118 to Spencer et al.

U.S. Pat. No. 7,018,406 to Seguin et al.

U.S. Pat. No. 6,458,153 and US Patent Application Publication 2003/0023300 to Bailey et al.

US Patent Application Publication 2004/0186563 to Lobbi

US Patent Application Publication 2003/0130729 to Paniagua et al.

US Patent Application Publication 2004/0236411 to Sarac et al.

US Patent Application Publication 2005/0075720 to Nguyen et al.

US Patent Application Publication 2006/0058872 to Salahieh et al.

US Patent Application Publication 2005/0137688 to Salahieh et al.

US Patent Application Publication 2005/0137690 to Salahieh et al.

US Patent Application Publication 2005/0137691 to Salahieh et al.

US Patent Application Publication 2005/0143809 to Salahieh et al.

US Patent Application Publication 2005/0182483 to Osborne et al.

US Patent Application Publication 2005/0137695 to Salahieh et al.

US Patent Application Publication 2005/0240200 to Bergheim

US Patent Application Publication 2006/0025857 to Bergheim et al.

US Patent Application Publication 2006/0025855 to Lashinski et al.

US Patent Application Publication 2006/0047338 to Jenson et al.

US Patent Application Publication 2006/0052867 to Revuelta et al.

US Patent Application Publication 2006/0074485 to Realyvasquez

US Patent Application Publication 2003/0149478 to Figulla et al.

U.S. Pat. No. 7,137,184 to Schreck

U.S. Pat. No. 6,296,662 to Caffey

U.S. Pat. No. 6,558,418 to Carpentier et al.

U.S. Pat. No. 7,267,686 to DiMatteo et al.

SUMMARY OF THE INVENTION

In some embodiments of the present invention, a heart valve prosthesis comprises a collapsible support frame and a flexible prosthetic valve component. The support frame is shaped so as to define a downstream section to which the flexible prosthetic valve component is coupled, and an upstream inlet that is configured to apply an axial force in a downstream direction on an upstream side of the native annulus and left ventricular outflow tract (LVOT). The prosthesis is configured to be compressed partially within a delivery tube for transluminal delivery. The inlet is shaped such that when the prosthesis is compressed, an upstream portion of the inlet is tapered in an upstream direction toward a central longitudinal axis of the prosthesis. Upstream-most portions of the inlet converge to within 2 mm of the axis, e.g., within 1 mm of the axis, e.g., at the axis. Typically, all parts of the inlet within 1 mm of the upstream end of the inlet are within 2 mm of the axis, e.g., within 1 mm of the axis.

The tapered shape of the compressed inlet enables the delivery tube and prosthesis to pass smoothly through the native stenotic aortic valve, the vasculature, and, for some applications, through an introducer sheath. The tapered shape thus obviates the need for a separate tapered delivery cap that is coupled to the upstream end of the delivery tube while advancing of the delivery tube and prosthesis through the native stenotic aortic valve, vasculature, and/or introducer sheath. For some applications, without such a separate delivery cap, the delivery tube may be shorter than it would be with such a delivery cap, because at least a tapered portion of a separate delivery cap must be positioned in series with the compressed prosthesis on a delivery system. In addition, not requiring a separate delivery cap covering the compressed inlet can reduce the compressed diameter of the upstream-most tip of the prosthesis (such as by twice the diameter of the thickness of the wall of the delivery tube).

For some applications, a small delivery tip is removably coupled to the upstream-most portions of the inlet, and not coupled to the delivery tube. The tip covers the upstream-most portions, which may be sharp. The tip is shaped so as to define a longitudinal opening therethrough, through which a guidewire passes during the delivery procedure.

There is therefore provided, in accordance with an embodiment of the present invention, apparatus including a valve prosthesis for attachment to a native valve complex of a subject, the prosthesis configured to assume a compressed delivery state and an uncompressed implantation state, the prosthesis including:

a support frame, which is shaped so as to define an upstream inlet having upstream-most portions that are tapered in an upstream direction toward a central longitudinal axis of the prosthesis when the prosthesis assumes the compressed delivery state; and a flexible prosthetic heart valve component, coupled to the support frame.

Typically, the upstream inlet has a greatest outer inlet diameter of at least 20 mm when the prosthesis assumes the uncompressed implantation state.

For some applications, the support frame is shaped so as to define a downstream section that is configured to apply an upstream axial force to a downstream side of the native valve complex, the upstream inlet is configured to apply a downstream axial force on an upstream side of the native valve complex, and the valve prosthesis is configured such that the upstream and downstream axial forces together anchor the valve prosthesis to the native valve complex.

In an embodiment, the upstream-most portions of the inlet converge to within 2 mm of the central longitudinal axis when the prosthesis assumes the compressed delivery state. For some applications, the upstream-most portions of the inlet converge at the central longitudinal axis when the prosthesis assumes the compressed delivery state. For some applications, at least one the upstream-most portions of the inlet converges at the central longitudinal axis when the prosthesis assumes the compressed delivery state.

In an embodiment, all parts of the inlet within 1 mm of an upstream end of the inlet are within 2 mm of the central longitudinal axis when the prosthesis assumes the compressed delivery state.

In an embodiment, the apparatus further includes a delivery tube, and the prosthesis is configured to assume the compressed delivery state upon placement of the valve prosthesis partially within the delivery tube. For some applications, the delivery tube is configured to prevent full insertion of the valve prosthesis into the delivery tube. Alternatively or additionally, the valve prosthesis has a marking that indicates a desired depth of insertion in a downstream direction of the valve prosthesis into the delivery tube.

For some applications, when the prosthesis assumes the compressed delivery state, a portion of the inlet that extends outside of the delivery tube has a greatest outer inlet diameter that is greater than an outer tube diameter of the delivery tube. For other applications, when the prosthesis assumes the compressed delivery state, a portion of the inlet that extends outside of the delivery tube has a greatest outer inlet diameter that is equal to an outer tube diameter of the delivery tube.

For some applications, when the prosthesis assumes the uncompressed implantation state, the support frame is shaped so as to define two curved portions connected by an intermediary portion, shaped such that when the intermediary portion is subjected to an upstream axial force applied by the delivery tube when the prosthesis is placed partially within the delivery tube, resulting vector component forces compress the upstream inlet toward the central longitudinal axis.

There is further provided, in accordance with an embodiment of the present invention, apparatus including:
 a delivery tube; and
 a valve prosthesis for attachment to a native valve complex of a subject, the prosthesis configured to assume a compressed delivery state when placed partially within the delivery tube, and to assume an uncompressed implantation state when removed from the delivery tube, the prosthesis including:
 a support frame, which extends partially outside of the delivery tube in an upstream direction when the prosthesis assumes the compressed delivery state; and
 a flexible prosthetic heart valve component, coupled to the support frame.

In an embodiment, the support frame is shaped so as to define an upstream inlet, at least a portion of which extends outside of the delivery tube. For some applications, the portion of the upstream inlet that extends outside of the delivery tube has an axial length that is greater than 20% of an axial length of the support structure when the valve prosthesis assumes the compressed delivery state. Typically, the upstream inlet has a greatest outer inlet diameter of at least 20 mm when the prosthesis assumes the uncompressed implantation state. For some applications, the upstream inlet has a greatest outer inlet diameter that is no greater than 6 mm when the prosthesis assumes the compressed delivery state.

For some applications, the support frame is shaped so as to define a downstream section that is configured to apply an upstream axial force to a downstream side of the native valve complex, the upstream inlet is configured to apply a downstream axial force on an upstream side of the native valve complex, and the valve prosthesis is configured such that the upstream and downstream axial forces together anchor the valve prosthesis to the native valve complex.

For some applications, the entire upstream inlet extends outside of the delivery tube.

In an embodiment, the portion of the upstream inlet has a greatest outer inlet diameter that is equal to an outer tube diameter of the delivery tube, when the prosthesis assumes the compressed delivery state when placed partially within the delivery tube. In an embodiment, the portion of the upstream inlet has a greatest outer inlet diameter that is greater than an outer tube diameter of the delivery tube, when the prosthesis assumes the compressed delivery state when placed partially within the delivery tube. For some applications, the apparatus further includes an introducer sheath into which the delivery tube and valve prosthesis are placed, the introducer sheath having an inner sheath diameter less than the greatest outer inlet diameter (a) when the prosthesis assumes the compressed delivery state when placed partially within the delivery tube, and (b) before the valve prosthesis is placed into the introducer sheath. For some applications, the inner sheath diameter no greater than 0.2 mm greater than the outer tube diameter.

In an embodiment, the portion of the inlet has a diameter that first increases along an upstream direction, and subsequently monotonically decreases along the upstream direction, when the prosthesis assumes the compressed delivery state when placed partially within the delivery tube. For some applications, the upstream inlet has upstream-most elements that converge within 2 mm of a central longitudinal axis of the valve prosthesis when the prosthesis assumes the compressed delivery state when placed partially within the delivery tube. For some applications, the prosthesis is shaped so as to define a downstream section, and a throat section between the downstream section and the portion of the inlet, and a diameter of the prosthesis, when it assumes the compressed delivery state when placed partially within the delivery tube, decreases in the upstream direction from the downstream section to the throat section, and increases in the upstream direction from the throat section to the portion of the inlet.

In an embodiment, the upstream inlet has upstream-most elements, and the apparatus further includes a neutral tube that is concentric with the delivery tube, and the valve prosthesis is partially held between the delivery tube and the neutral tube when the valve prosthesis assumes the compressed delivery state when partially placed in the delivery tube; and a delivery tip, which is removably coupled to the neutral tube, and not coupled to the delivery tube, such that the upstream-most elements of the inlet rest against a downstream side of the delivery tip when the prosthesis assumes the collapsed delivery state. For some applications, the delivery tip has a length of less than 10 mm, and a maximum diameter of less than 4 mm. For some applications, the upstream-most elements are tapered in an upstream direction toward a central longitudinal axis of the prosthesis when the prosthesis assumes the compressed delivery state when placed partially within the delivery tube.

In an embodiment, the upstream inlet has upstream-most elements that are tapered in an upstream direction toward a central longitudinal axis of the prosthesis when the prosthesis assumes the compressed delivery state when placed partially within the delivery tube. For some applications, when the prosthesis assumes the uncompressed implantation state, the support frame is shaped so as to define two curved portions connected by an intermediary portion, shaped such that when the intermediary portion is subjected to an upstream axial force applied by the delivery tube when the prosthesis is placed partially within the delivery tube, resulting vector component forces compress the upstream inlet toward the central longitudinal axis.

There is still further provided, in accordance with an embodiment of the present invention, a method including:
 providing a valve prosthesis for attachment to a native valve complex of a subject, the prosthesis configured to assume a compressed delivery state and an uncompressed implantation state, the prosthesis including (a) a support frame, which is shaped so as to define an upstream inlet, and (b) a flexible prosthetic heart valve component, coupled to the support frame; and
 causing the valve prosthesis to assume the compressed delivery state by inserting the valve prosthesis at least partially into a delivery tube, such that upstream-most portions of the upstream inlet taper in an upstream direction toward a central longitudinal axis of the prosthesis.

There is additionally provided, in accordance with an embodiment of the present invention, a method including:
 providing a valve prosthesis for attachment to a native valve complex of a subject, the prosthesis configured to assume a compressed delivery state when placed partially within the delivery tube, and to assume an uncompressed implantation state when removed from the delivery tube, the prosthesis including (a) a support frame, and (b) a flexible prosthetic heart valve component, coupled to the support frame; and causing the valve prosthesis to assume the compressed delivery state by inserting the valve prosthesis partially into the delivery tube such that the support frame extends partially outside of the delivery tube in an upstream direction.

In an embodiment, the support frame is shaped so as to define an upstream inlet, and inserting includes inserting the valve prosthesis partially into the delivery tube such that at least a portion of the upstream inlet extends outside of the delivery tube.

In an embodiment, the method further includes placing the delivery tube and valve prosthesis into an introducer sheath that has an inner sheath diameter less than the greatest outer inlet diameter (a) when the prosthesis assumes the compressed delivery state when placed partially within the delivery tube, and (b) before the valve prosthesis is placed into the introducer sheath. For some applications, the inner sheath diameter no greater than 0.2 mm greater than the outer tube diameter.

In an embodiment, inserting includes inserting the valve prosthesis partially into the delivery tube such that the valve prosthesis is partially held between the delivery tube and a neutral tube that is concentric with the delivery tube, and the method further includes removably coupling a delivery tip to the neutral tube without coupling the delivery tip to the delivery tube, such that upstream-most elements of the inlet rest against a downstream side of the delivery tip when the prosthesis assumes the collapsed delivery state. For some applications, the delivery tip has a length of less than 10 mm, and a maximum diameter of less than 4 mm. For some applications, inserting includes inserting the valve prosthesis partially into the delivery tube such that the upstream-most elements are tapered in an upstream direction toward a central longitudinal axis of the prosthesis.

In an embodiment, the method further includes delivering the valve prosthesis to the native valve complex while the valve prosthesis is partially inserted into the delivery tube such that the support frame extends partially outside of the delivery tube in the upstream direction.

The present invention will be more fully understood from the following detailed description of embodiments thereof, taken together with the drawings, in which:

BRIEF DESCRIPTION OF THE DRAWINGS

FIGS. 3A-C are schematic cross-sectional illustrations of the valve prosthesis of FIGS. 1A-C in a compressed delivery state partially within a delivery tube, in accordance with respective embodiments of the present invention;

FIGS. 4A and 4B are schematic illustrations showing the valve prosthesis of FIGS. 1A-C in partially-compressed and compressed states, respectively, in accordance with an embodiment of the present invention;

FIG. 7 is a schematic illustration of a balloon-inflatable valve prosthesis, in accordance with an embodiment of the present invention.

DETAILED DESCRIPTION OF THE PREFERRED EMBODIMENT

Figure 1A:
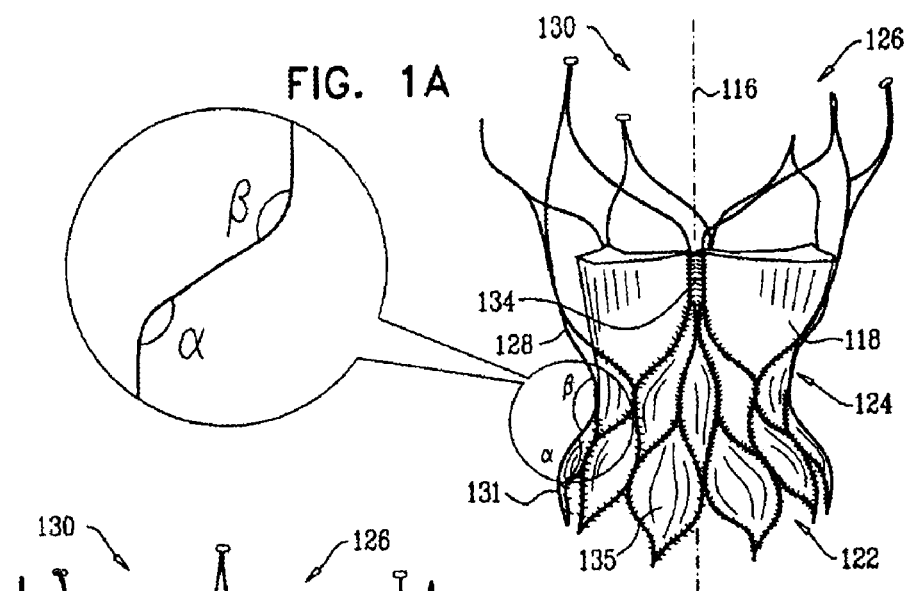
FIGS. 1A-C are schematic illustrations of a valve prosthesis, in accordance with an embodiment of the present invention.
Figure 1B:
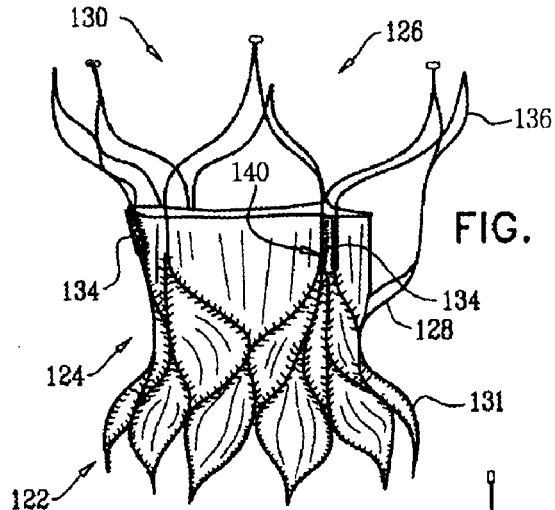
Figure 1C:
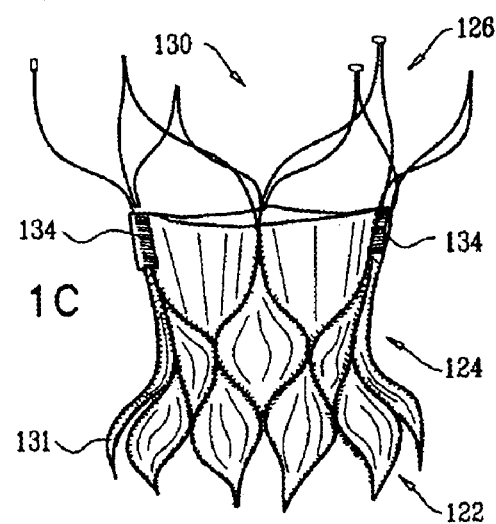

FIGS. 1A and 1B are schematic illustrations of a valve prosthesis 130, in accordance with an embodiment of the present invention. FIG. 1A shows the prosthesis including a flexible prosthetic downstream valve component 118 and a inlet covering 135 that covers an upstream inlet 131, while FIGS. 1B and 1C, for clarity of illustration, show only a support frame 140 of the valve prosthesis, without flexible prosthetic downstream valve component 118 or inlet covering 135. Valve prosthesis 130 comprises a collapsible support frame 140, which typically comprises exactly three commissural posts 134, arranged circumferentially around a central longitudinal axis 116 of the valve prosthesis. Valve prosthesis 130 further comprises flexible prosthetic downstream valve component 118 coupled to commissural posts 134. Valve component 118 typically comprises a pliant material. The pliant material is configured to collapse inwardly (i.e., towards the central longitudinal axis) during diastole, in order to inhibit retrograde blood flow, and to open outwardly during systole, to allow blood flow through the prosthesis.

Valve prosthesis 130 is configured to be implanted in a native diseased valve of a patient, such as a native stenotic aortic or pulmonary valve, using a minimally-invasive approach, such as a beating heart endovascular retrograde transaortic, e.g. transfemoral, procedure. Support frame 140 is typically compressed so that its diameter is reduced in order to facilitate loading into a delivery tube, and, optionally, an introducer sheath, for delivery to the native valve site during a minimally-invasive delivery procedure, as described hereinbelow with reference to FIGS. 2A-B, 3A-C, 4A-B, 5A-C, and 6A-B. Support frame 140 is configured such that application of radial forces thereon radially compress the frame, reducing the frame's outer diameter. Upon removal of the radial forces, the frame assumes its previous uncompressed diameter and shape, i.e., the frame is self-expanding. The prosthesis is compressed by loading it into a delivery tube sufficiently small to allow transluminal delivery to the patient's native valve site. Support frame 140 comprises a suitable material that allows mechanical deformations associated with crimping and expansion of valve prosthesis 130, such as, but not limited to, a superelastic material, such as nitinol, or a stainless steel alloy (e.g., AISI 316).

Support frame 140 is typically shaped to define an upstream section 122, a throat section 124, and a downstream section 126. The cross-sectional area of upstream section 122 gradually decreases from an upstream end thereof to a downstream end adjacent to throat section 124. The cross-sectional area of throat section 124 is typically less than that of the aortic annulus of the intended patient. The cross-sectional area of downstream section 126 gradually increases to an area greater than that of throat section 124. Thus the cross-sectional areas of both the upstream and downstream sections are greater than that of the throat section. Throat section 124 is configured to be placed within the leaflet section of the native valve, slightly above the aortic annulus at the ventriculo-aortic border, such that downstream section 126 is located in the aorta, such as in the aortic sinuses. Typically, throat section 124 is configured to exert an outward radial force against the native leaflets, in order to prevent blood leakage between the valve prosthesis and the native valve. Such outward radial force typically does not substantially aid with fixation of the valve prosthesis at the native valve complex, and typically does not radially squeeze the native leaflets between the throat section and any other elements of valve prosthesis 130.

Typically, support frame is elastic, and is shaped so as to define a plurality of collapsible cells. For example, the support frame may be fabricated by cutting a solid tube. The cells may be diamond-shaped, parallelogram-shaped, or otherwise shaped to be conducive to crimping the frame. Downstream section 126 is shaped so as to define upstream inlet 131, which is configured to apply an axial force directed toward the ascending aorta. Typically, when prosthesis 130 assumes an uncompressed implantation state, upstream inlet 131 has a greatest diameter of at least 20 mm, such as at least 26 mm, and of no more than 32 mm, such as no more than 30 mm. Optionally, inlet 131 is shaped so as to define one or more barbs positioned circumferentially such that the barbs pierce the native vale annulus in order to provide better anchoring (configuration not shown). Typically, valve prosthesis 130 further comprises inlet covering 135 which is coupled to upstream inlet 131, such as by sewing the covering within the inlet (configuration shown in FIG. 1A) or around the inlet (configuration not shown). Inlet covering 135 may comprise, for example, polyester or a processed biological material, such as pericardium. Support frame 140 thus defines a central structured body for flow passage that terminates in an upstream direction in a flared inlet (upstream inlet 131) that is configured to be seated within an LVOT immediately below an aortic annulus/aortic valve. Typically, the upstream axial force applied by downstream section 126 and the downstream axial force applied by upstream inlet 131 together anchor valve prosthesis 130 to the native valve complex.

In an embodiment of the present invention, support frame 140 is shaped so as to define a plurality of downstream axial support extensions 128, such as described in a US provisional patent application to Tuval et al., filed Sep. 15, 2008, entitled, "Prosthetic heart valve for transfemoral delivery," which is assigned to the assignee of the present application and is incorporated herein by reference. The downstream axial support extensions join a downstream side of upstream inlet 131, and extend in a downstream direction at a first angle with respect to the central longitudinal axis of valve prosthesis 130, while commissural posts 134 extend in a downstream direction at a second angle with respect to axis 116. The first angle is greater than the second angle. Because of this greater angle, downstream axial support extensions 128: (a) apply an upstream axial force to a downstream side of the native leaflet tips, (b) do not touch the leaflets of the flexible prosthetic valve component when the prosthetic valve component is in its open position, and (c) provide stability to support frame 140. The first angle may, for example, be between about 15 and about 45 degrees, such as about 130 degrees, while the second angle may, for example, be between about 1 and about 15 degrees, such as about 8 degrees.

For some applications, support frame 140 is shaped so as to define a plurality of upper sinus support elements 136, which extend in a downstream direction. Upper sinus support elements 136 are configured to rest against the upper aortic sinuses (i.e., the downstream portion of the aortic sinuses) upon implantation of valve prosthesis 130, so as to provide support against tilting of the prosthesis with respect to the central longitudinal axis thereof. Typically, the downstream-most portions of upper sinus support elements 136 are bent toward the central longitudinal axis of the prosthesis to avoid damage to the walls of the upper sinuses. For some applications, support frame 140 is shaped so as to define exactly three downstream axial support extensions 128 and exactly six upper sinus support elements 136.

In an embodiment of the present invention, a portion of the cells of support frame 140 are shaped to define a plurality of outwardly-extending short axial support arms, which extend radially outward and upstream from the central longitudinal axis of valve prosthesis 130, such as described in U.S. Provisional Application 60/978,794, filed Oct. 10, 2007, entitled, "Prosthetic heart valve specially adapted for transfemoral delivery," and the above-mentioned U.S. provisional application to Tuval et al., both of which are assigned to the assignee of the present application and are incorporated herein by reference.

Although exactly three commissural posts 134 are shown in the figures, for some applications valve prosthesis 130 comprises fewer or more posts 134, such as two posts 134, or four or more posts 134. It is noted that approximately 90% of humans have exactly three aortic sinuses. The three posts provided in most embodiments correspond to these three aortic sinuses. For implantation in the approximately 10% of patients that have exactly two aortic sinuses, prosthesis 130 typically includes exactly two posts.

Figure 2A:
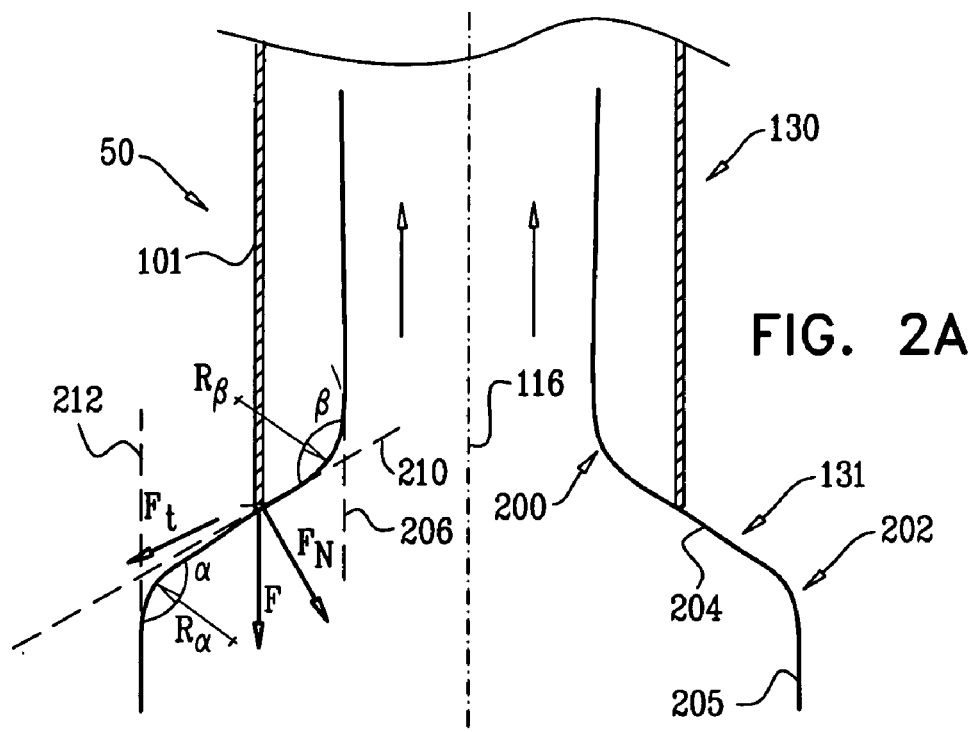
FIGS. 2A and 2B are schematic cross-sectional illustrations of the valve prosthesis of FIGS. 1A-C in an uncompressed implantation state and a partially-compressed delivery state, respectively, in accordance with an embodiment of the present invention.
Figure 2B:
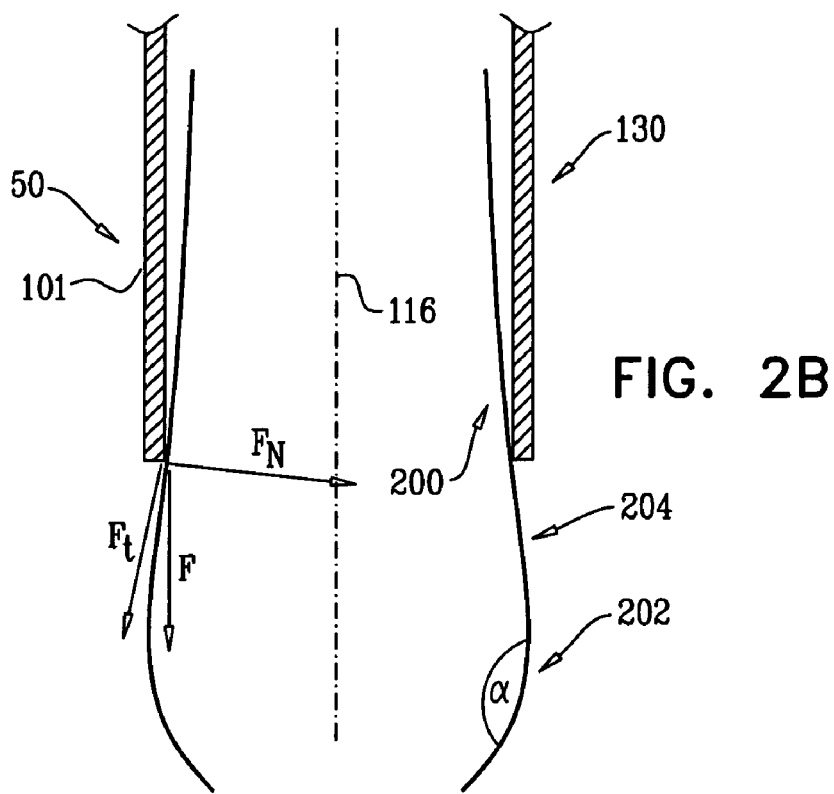

FIGS. 2A and 2B are schematic cross-sectional illustrations of valve prosthesis 130 in an uncompressed implantation state and a partially-compressed delivery state, respectively, in accordance with an embodiment of the present invention. In the uncompressed implantation state, upstream inlet 131 generally assumes the shape of a bell characterized a first downstream curved portion 200 and a second upstream curved portion 202, which are connected by an intermediary portion 204, which may be straight (as shown in FIGS. 2A and 2B) or slightly curved (configuration not shown). An upstream-most portion 205 of the inlet extends in an upstream direction from second upstream curved portion 202. A delivery system 50 for delivering valve prosthesis 130 to a target site and implanting the prosthesis at the site comprises a delivery tube 101.

As shown in FIG. 2A, first curved portion 200 curves outwardly from central longitudinal axis 116 of prosthesis 130 (which coincides with the central longitudinal axis of delivery tube 101), while second curved portion 202 curves inwardly toward the axis, typically such that upstream-most portion 205 is parallel to axis 116. At first curved portion 200, (a) a first line 206 parallel to central longitudinal axis 116 defines an angle $\beta$ with respect to (b) a second line 210 that is tangential to both curved portions 200 and 202. Angle $\beta$ is typically between about 90 and about 170 degrees, such as between about 100 and about 135 degrees. First curved portion 200 typically has a radius of curvature $R\beta$ of between about 1 and about 15 mm, such as between about 4 and about 10 mm. At second curved portion 202, (a) a third line 212 generally parallel with upstream-most portion 205 defines an angle $\alpha$ with respect to (b) second line 210. Angle $\alpha$ is typically between about 90 and about 170 degrees, such as between about 100 and about 135 degrees. Second curved portion 202 typically has a radius of curvature $R\alpha$ of between about 1 and about 15 mm, such as between about 4 and about 10 mm.

As prosthesis 130 is retracted into a delivery tube 101, the tube exerts a force F on intermediary portion 204 of the inlet. Force F has two force vector components: (1) Ft, which acts in a direction generally parallel to portion 204, and (2) Fn, which acts in a direction generally orthogonal to portion 204.

In the partially-compressed state shown in FIG. 2B, delivery tube 101 thus forces the inlet to bend around first curved portion 200, thus moving the portion of the inlet upstream to the point at which delivery tube 101 applies force F toward central longitudinal axis 116. The shape of the fully compressed upstream portion inlet (as shown, for example, in FIGS. 3A-C) depends in large part on the curvature of curved portion 202.

Reference is made to FIGS. 3A-C, which are schematic cross-sectional illustrations of valve prosthesis 130 in the compressed delivery state partially within delivery tube 101, in accordance with respective embodiments of the present invention. Delivery system 50 further comprises a valve holder 104 and a neutral tube 103 that is concentric with delivery tube 101. Valve prosthesis 130 is partially held between delivery tube 101 and neutral tube 103. Delivery system 50 is used to effect the release of valve prosthesis 130 by moving delivery tube 101 with respect to neutral tube 103.

Valve prosthesis 130 is configured to assume its compressed delivery state upon being placed partially within delivery tube 101, such that support frame 140 extends at least partially outside of the delivery tube in an upstream direction. Typically, at least a portion of upstream inlet 131 extends outside of the delivery tube. For example, the portion of the upstream inlet that extends outside of the delivery tube may have an axial length that is greater than 20% of an axial length of the support structure when the valve prosthesis assumes the compressed delivery state. Optionally, the entire upstream inlet extends outside of the delivery tube. Providing an appropriate angle a and an appropriate radius of curvature Rα ensures that the upstream-most portions of the compressed inlet converge towards central longitudinal axis 116, rather than being oriented generally parallel with the axis.

Typically, upstream-most portions 246 of the inlet converge to within 2 mm of the axis, such as within 1 mm of the axis. For some applications, one or more (e.g., all) of the upstream-most portions of the inlet converge at the axis. (The upstream-most portions typically comprise cells of frame 140.) For some applications, as shown in the figures, the upstream ends of inlet 131 rest against neutral tube 103. Typically, all parts of the inlet within 1 mm of the upstream end of the inlet are within 2 mm of the axis, such as within 1 mm of the axis. For some applications, upstream inlet 131 has a greatest outer diameter that is no greater than 6 mm, such as no greater than 4.5 mm, when the prosthesis assumes the compressed delivery state.

For some applications, delivery tube 101 is configured to aid in properly positioning valve prosthesis 130 partially within the delivery tube at a desired depth of insertion. The delivery tube may comprise or be shaped so as to define a stopper portion 132, typically at a downstream end of the tube, that blocks further insertion of the prosthesis into the delivery tube. For example, valve holder 104 may be configured to come in contact with stopper portion 132. Alternatively or additionally, valve prosthesis 130 has a marking 138 that indicates a desired depth of insertion in a downstream direction of the valve prosthesis into the delivery tube.

A diameter of a downstream portion 244 of inlet 131 outside of delivery tube 101 increases along an upstream direction (towards the right in FIGS. 3A-C), while a diameter of upstream-most portions 246 of the inlet monotonically decreases along the upstream direction, i.e., tapers inwardly toward central longitudinal axis 116.

For some applications, such as in the configuration shown in FIG. 3A, a greatest outer diameter DS of inlet 131 is greater than or equal to an outer diameter DO of delivery tube 101, when the prosthesis assumes the compressed delivery state. This wide portion of the inlet prevents direct exposure of the upstream end of delivery tube 101 (which may be sharp) to the vasculature, the native stenotic aortic valve, and an introducer sheath (as described hereinbelow), as the delivery tube and the prosthesis are advanced toward the implantation site. In addition, because outer diameter DO of delivery tube 101 is greater than an inner diameter DI thereof, this wide portion of the inlet need not be compressed as much as would be necessary if it were to be inserted into delivery tube 101. Furthermore, this bulging configuration (in which DS is greater than DO) enables the use of an introducer sheath (as described hereinbelow) having an internal diameter less than that of the bulging portion of the inlet, because the bulging portion of the compressed inlet (which is free of delivery tube 101) can be further radially compressed by insertion into the introducer sheath. When, during an implantation procedure, delivery tube 101 and valve prosthesis 130 exit the introducer sheath and enter the patient's blood vessel (typically the iliac artery), the vessel has a diameter greater than the diameter of the bulging portion of the crimped prosthesis, which allows this bulging portion to expand, without coming in contact with the wall of the vessel, which is larger at this point in this vasculature. An introducer sheath can be used that fits delivery tube 101, while allowing greatest outer diameter DS of inlet 131 to be greater than outer diameter DO of delivery tube 101.

For other applications, such as in the configuration shown in FIG. 3B, the portion of inlet 131 having the greatest diameter, when in its compressed delivery state, is within delivery tube 101, such that greatest outer inlet diameter DS is equal to inner diameter DI of delivery tube 101.

For still other applications, such as the configuration shown in FIG. 3C, greatest outer diameter DS of the downstream bulging portion is greater than outer diameter DO of delivery tube 101. An introducer sheath, as described hereinbelow, may still have an inner diameter equal to or only slightly larger than outer diameter DO of the delivery tube (e.g., less than 0.2 mm greater than DO, such as less 0.1 mm greater than DO), because insertion of the downstream bulging portion of the inlet into the introducer sheath compresses the bulging portion, completing the compression of the prosthesis, as described hereinbelow with reference to FIGS. 5A-C. Not compressing the inlet entirely within delivery tube 101 results in loading and unloading forces that are less would result if the inlet were inserted entirely into the delivery tube.

Reference is again made to FIGS. 3A-C. In an embodiment of the present invention, a small delivery tip 260 is removably coupled to neutral tube 103 such that the upstream-most portions of inlet 131 rest against a downstream side of the delivery tip when the prosthesis assumes the collapsed delivery state partially inserted in delivery tube 101. Delivery tip 260 is not coupled to delivery tube 101. The tip covers the upstream-most portions, which may be sharp. The delivery tip typically has a length of less than 10 mm, e.g., less than 5 mm, and a maximum diameter of less than 4 mm, e.g., less than 3 mm. The tip is shaped so as to define a longitudinal opening therethrough, through which a guidewire 242 slides during the delivery procedure. Typically, inlet tip 131 prevents the upstream-most ends of inlet 131 from scraping against the blood vessel or the introducer sheath. Although these upstream-most ends may rest against neutral tube 103, they may still scrape because of their thickness.

Reference is made to FIGS. 4A and 4B, which are schematic illustrations showing valve prosthesis 130 in partially-compressed and compressed states, respectively, in accordance with an embodiment of the present invention. In the compressed state shown in FIG. 4B, the greatest outer diameter of inlet 131 is equal to the outer diameter of delivery tube 101.

Figure 5A:
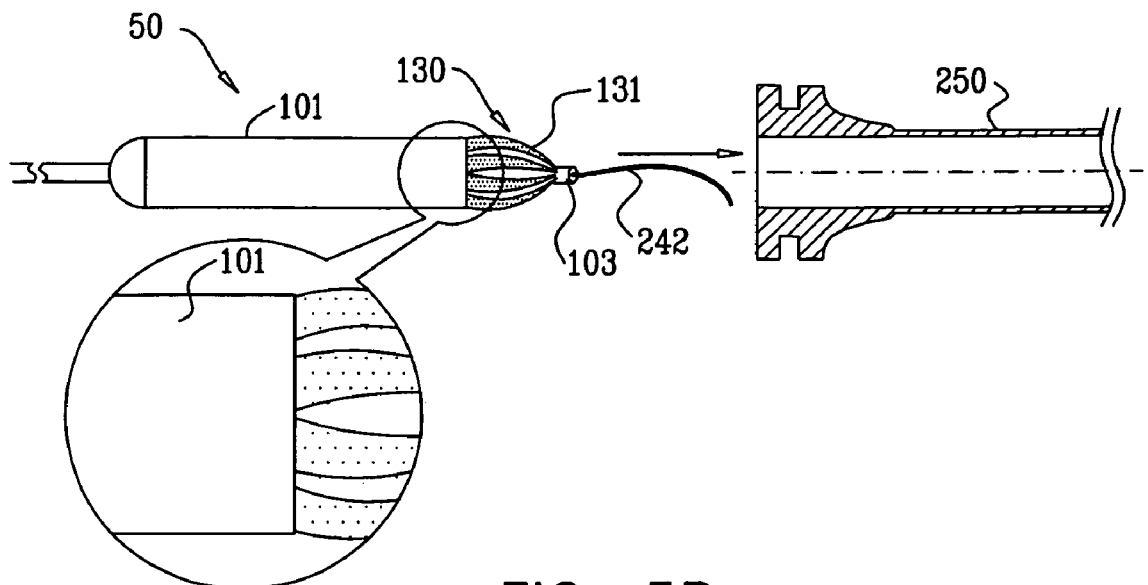
FIGS. 5A-C are schematic illustrations of the valve prosthesis of FIGS. 1A-C and a delivery tube in several stages of insertion into an introducer sheath, in accordance with an embodiment of the present invention.
Figure 5B:
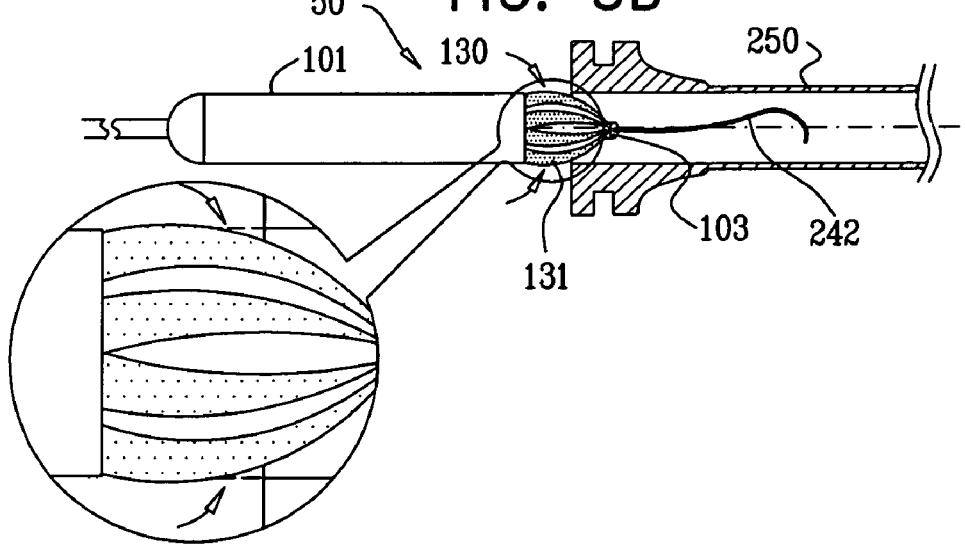
Figure 5C:
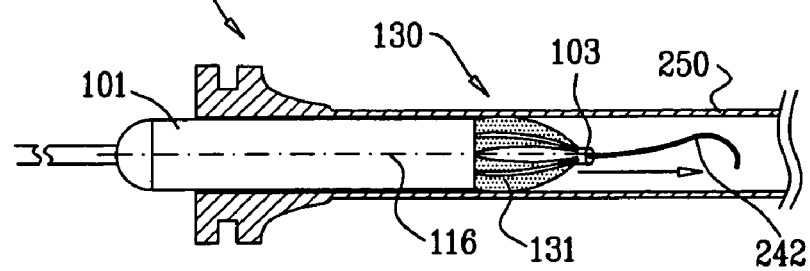

Reference is made to FIGS. 5A-C, which are schematic illustrations of valve prosthesis 130 and delivery tube 101 in several stages of insertion into an introducer sheath 250, in accordance with an embodiment of the present invention. In this embodiment, introducer sheath 250, such as a femoral introducer sheath, is provided for aiding delivery of valve prosthesis 130. The introducer sheath is used to advance delivery tube 101 and valve prosthesis 130 into the vasculature, and at least partially through the vasculature toward the ascending aorta. Typically, during an implantation procedure, the introducer sheath is inserted into the femoral artery, and advanced until a distal end of the sheath reaches the iliac artery, the descending aorta, or the ascending aorta. The valve prosthesis, which is loaded into the delivery tube, is then inserted into the sheath and advanced therethrough until it exits the distal end of the sheath in the iliac artery, descending aorta, or ascending aorta. The prosthesis and delivery tube are then further advanced until they reach the site of the native valve complex.

As in the configuration described hereinabove with reference to FIG. 3C, in the configuration shown in FIGS. 5A-C the greatest outer diameter of the downstream bulging portion of inlet 131 is greater than the outer diameter of delivery tube 101, when the prosthesis assumes the compressed delivery state and prior to its insertion into sheath 250, as shown in FIG. 5A. FIG. 5B shows inlet 131 partially inserted into the sheath, such that the inlet is partially compressed by the sheath. FIG. 5C shows inlet 131 fully inserted into the sheath, such that the greatest outer diameter of the inlet has been reduced to the inner diameter of the sheath, which is approximately equal to the outer diameter of delivery tube 101. Inlet 131 thus has a greatest outer diameter that is greater than the outer diameter of delivery tube 101 before the inlet is inserted into the sheath, and approximately the same as the outer diameter of delivery tube 101 after the inlet has been inserted into the sheath. After the prosthesis and delivery tube pass through the sheath and exit the distal end of the sheath, inlet 131 once again assumes an outer diameter greater than that of the delivery tube. (Upon release from delivery tube 101, inlet 131 assumes an even greater diameter for implantation at the native valve complex.)

Figure 6A:
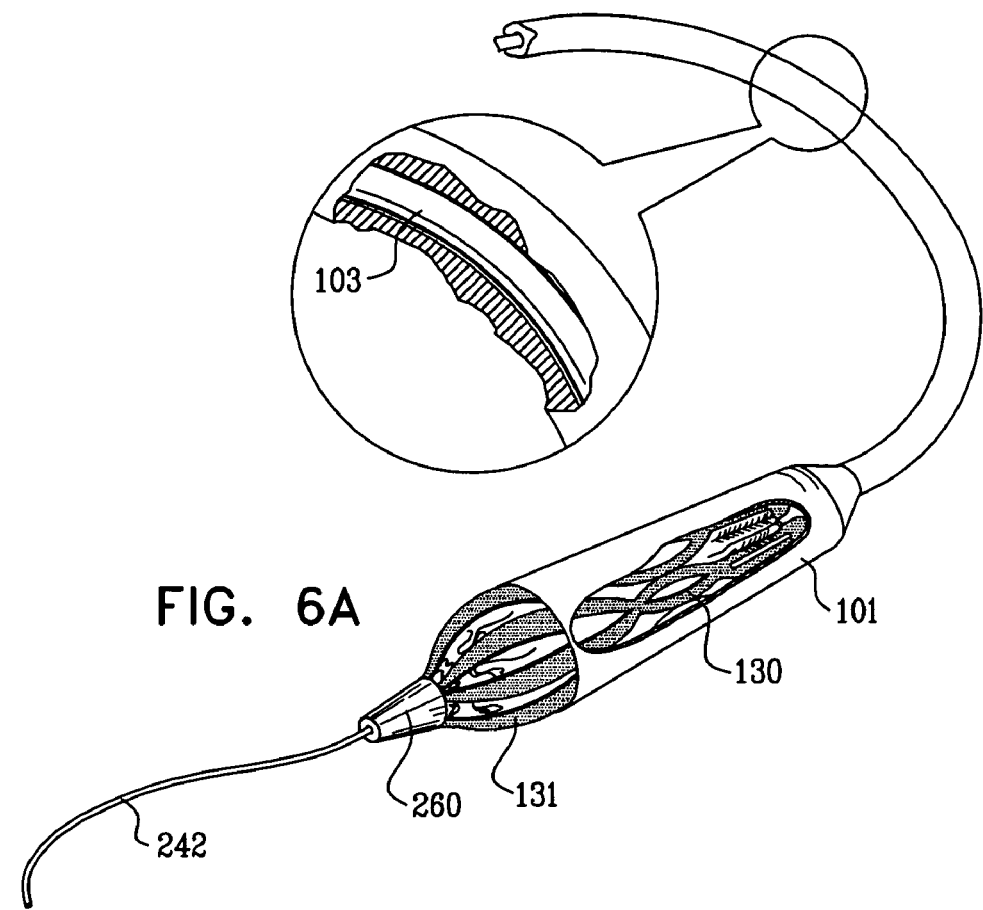
FIGS. 6A and 6B are perspective schematic illustrations of the prosthesis of FIGS. 1A-C in its compressed state, in accordance with respective embodiments of the present invention.
Figure 6B:
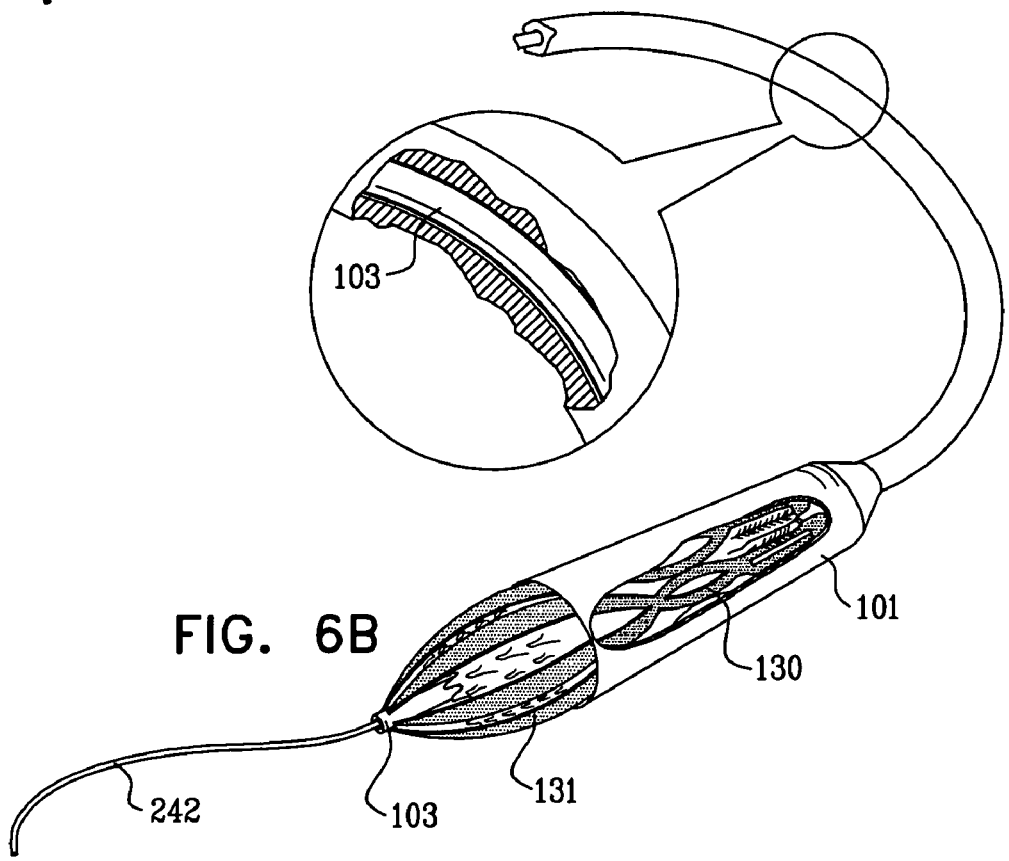

FIGS. 6A and 6B are perspective schematic illustrations of prosthesis 130 in its compressed state, in accordance with respective embodiments of the present invention. In the embodiment shown in FIG. 6A, delivery tip 260 is provided, as described hereinabove with reference to FIG. 3A-C. As can be seen, the delivery tip is not coupled to delivery tube 101. In the embodiment shown in FIG. 6B, the delivery tip is not provided. The upstream-most portions of inlet 131 converge toward a central longitudinal axis of the prosthesis, and rest against neutral or inner tube 103 of delivery system 50.

In an embodiment of the present invention, during an implantation procedure delivery tube 101 is inserted into a body lumen, such as a femoral artery, and guided over guidewire 242 through the ascending aorta and over an aortic arch, until the tip of the guidewire passes into a left ventricle. Optionally, the stenotic aortic valve is partially dilated to about 15-20 mm (e.g., about 16 mm), typically using a standard valvuloplasty balloon catheter. The upstream-most portion of valve prosthesis 130 is advanced past the native aortic valve leaflets into the left ventricle. At this stage of the procedure, delivery tube 101 is located between the native aortic leaflets.

Delivery tube 101 is withdrawn a predetermined distance to expose upstream inlet 131 of valve prosthesis 130. Delivery tube 101 moves with respect to inner tube 103, such that valve prosthesis 130 and inner tube 103 are partially exposed from the catheter. Inlet 131 is positioned within the left ventricle.

Delivery tube 101 is withdrawn until inlet 131 abuts firmly against the ventricular side of the aortic annulus and/or the aortic valve leaflets. Delivery tube 101 is further withdrawn until the tube is located just upstream of the ends of commissural posts 134 of valve prosthesis 130, such that the commissural posts are still held firmly by delivery tube 101. Valve prosthesis 130 is completely released from delivery tube 101. Support frame 140, which is typically superelastic, rapidly expands to its fully opened position, pushing the native valve leaflets radially outward. Prosthetic valve 130 is thus released with the delivery tube being moved in only one direction during the entire procedure, which facilitates the implantation procedure significantly.

For some applications, prosthesis 130 is implanted using some of the techniques described with reference to FIGS. 9A-G in U.S. Application No. 2009-0240320A1 which is incorporated herein by reference, and/or using some of the techniques described in the above-mentioned U.S. provisional application to Tuval et al.

FIG. 7 is a schematic illustration of a balloon-inflatable valve prosthesis 330, in accordance with an embodiment of the present invention. In this embodiment; delivery system 50 comprises a shaped balloon 332 for plastically deforming a support structure 340 of valve prosthesis 330, to give the structure a non-cylindrical shape. In this embodiment, support structure 340 may comprise a stainless steel alloy which is plastically deformed during compression, thereby reducing the valve diameter, and mounted onto the balloon prior to implantation. When the delivery catheter is in place in the patient, shaped balloon 332 is used to open the compressed prosthesis into place, and to give it a non-cylindrical shape. The prosthesis is configured to be compressed partially within a delivery tube for transluminal delivery. An upstream inlet 331 of the prosthesis is shaped such that when the prosthesis is compressed partially within delivery tube 101, an upstream portion of the inlet is tapered in an upstream direction toward central longitudinal axis 116 of the prosthesis. Upstream-most portions of the inlet converge to within 2 mm of the axis, e.g., within 1 mm of the axis, e.g., at the axis. Typically, all parts of the inlet within 1 mm of the upstream end of the inlet are within 2 mm of the axis, e.g., within 1 mm of the axis.

In the present patent application, including in the claims, the word "downstream" means near or toward the direction in which the blood flow is moving, and "upstream" means the opposite direction. For embodiments in which the valve prosthesis is implanted at the aortic valve, the aorta is downstream and the ventricle is upstream. As used in the present patent application, including in the claims, the "native valve complex" includes the native semilunar valve leaflets, the annulus of the valve, the subvalvular tissue on the ventricular side, and the lower half of the semilunar sinuses. As used in the present application, including in the claims, a "native semilunar valve" is to be understood as including: (a) native semilunar valves that include their native leaflets, and (b) native semilunar valves, the native leaflets of which have been surgically excised or are otherwise absent.

Although prosthesis 130 is generally described herein as being implanted in an aortic position, the techniques described herein, as appropriately modified, may also be used to implant the prosthesis in other locations, such as in a pulmonary valve.

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

U.S. patent application Ser. No. 11/024,908, filed Dec. 30, 2004, entitled, "Fluid flow prosthetic device," which issued as U.S. Pat. No. 7,201,772;

International Patent Application PCT/IL2005/001399, filed Dec. 29, 2005, entitled, "Fluid flow prosthetic device," which published as PCT Publication WO 06/070372;

International Patent Application PCT/IL2004/000601, filed Jul. 6, 2004, entitled, "Implantable prosthetic devices particularly for transarterial delivery in the treatment of aortic stenosis, and methods of implanting such devices," which published as PCT Publication WO 05/002466, and U.S. patent application Ser. No. 10/563,384, filed Apr. 20, 2006, in the national stage thereof, which published as US Patent Application Publication 2006/0259134;

U.S. Provisional Application 60/845,728, filed Sep. 19, 2006, entitled, "Fixation member for valve";

U.S. Provisional Application 60/852,435, filed Oct. 16, 2006, entitled, "Transapical delivery system with ventriculo-arterial overflow bypass";

U.S. application Ser. No. 11/728,253, filed Mar. 23, 2007, entitled, "Valve prosthesis fixation techniques using sandwiching";

International Patent Application PCT/IL2007/001237, filed Oct. 16, 2007, entitled, "Transapical delivery system with ventriculo-arterial overflow bypass," which published as PCT Publication WO 2008/047354;

U.S. application Ser. No. 12/050,628, filed Mar. 18, 2008, entitled, "Valve suturing and implantation procedures";

a U.S. provisional application filed Sep. 15, 2008, entitled, "Prosthetic heart valve having identifiers for aiding in radiographic positioning";

U.S. Provisional Application 60/978,794, filed Oct. 10, 2007, entitled, "Prosthetic heart valve specially adapted for transfemoral delivery";

a U.S. provisional application filed Sep. 15, 2008, entitled, "Prosthetic heart valve for transfemoral delivery";

U.S. application Ser. No. 12/248,776, filed Oct. 9, 2008, entitled, "Prosthetic heart valve for transfemoral delivery."

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

It is understood that the examples and embodiments described herein are for illustrative purposes only and that various modifications or changes in light thereof will be suggested to persons skilled in the art and are to be included within the spirit and purview of this application and scope of any appended claims. All figures, tables, and appendices, as well as publications, patents, and patent applications, cited herein are hereby incorporated by reference in their entirety for all purposes.

What is claimed is:

1. Assembly for delivering an aortic valve prosthesis through the vasculature of a subject, the assembly comprising:
a delivery tube; and
the valve prosthesis for attachment to a native aortic valve complex of a subject, the prosthesis configured to assume a compressed delivery state when placed partially within the delivery tube and while being passed through at least a portion of the vasculature of the subject that is remote from the aortic valve complex of the subject, and to assume an uncompressed implantation state when removed from the delivery tube, the prosthesis comprising:
a support frame, which extends partially outside of the delivery tube when the prosthesis assumes the compressed delivery state and while being passed through at least a portion of the vasculature of the subject that is remote from the aortic valve complex of the subject; and
a flexible prosthetic heart valve component, coupled to the support frame,
wherein the support frame is shaped so as to define an upstream inlet with respect to blood flow during systole, at least a portion of which extends outside of the delivery tube, and
wherein the upstream inlet comprises upstream-most portions that are tapered in an upstream direction toward a central longitudinal axis of the prosthesis when the prosthesis assumes the compressed delivery state.

2. The assembly according to claim 1, wherein the support frame has an axial length, and
wherein the portion of the upstream inlet that extends outside of the delivery tube has an axial length that is greater than 20% of an axial length of the support frame when the valve prosthesis assumes the compressed delivery state.

3. The assembly according to claim 1, wherein the upstream inlet has a greatest outer inlet diameter of at least 20 mm when the prosthesis assumes the uncompressed implantation state.

4. The assembly according to claim 1, wherein the upstream inlet has a greatest outer inlet diameter that is no greater than 6 mm when the prosthesis assumes the compressed delivery state.

5. The assembly according to claim 1,
wherein the support frame is shaped so as to define a downstream section that is configured to apply an upstream axial force to a downstream side of the native valve complex,
wherein the upstream inlet is configured to apply a downstream axial force on an upstream side of the native valve complex, and
wherein the valve prosthesis is configured such that the upstream and downstream axial forces together anchor the valve prosthesis to the native valve complex.

6. The assembly according to claim 1, wherein the entire upstream inlet extends outside of the delivery tube.

7. The assembly according to claim 1, wherein the portion of the upstream inlet has a greatest outer inlet diameter that is equal to an outer tube diameter of the delivery tube, when the prosthesis assumes the compressed delivery state when placed partially within the delivery tube.

8. The assembly according to claim 1, wherein the portion of the upstream inlet has a greatest outer inlet diameter that is greater than an outer tube diameter of the delivery tube, when the prosthesis assumes the compressed delivery state when placed partially within the delivery tube.

9. Assembly for delivering an aortic valve prosthesis through the vasculature of a subject, the assembly comprising:
a delivery tube; and the valve prosthesis for attachment to a native aortic valve complex of a subject, the prosthesis configured to assume a compressed delivery state when placed partially within the delivery tube and while being passed through at least a portion of the vasculature of the subject that is remote from the aortic valve complex of the subject, and to assume an uncompressed implantation state when removed from the delivery tube, the prosthesis comprising:

a support frame, which extends partially outside of the delivery tube when the prosthesis assumes the compressed delivery state and while being passed through at least a portion of the vasculature of the subject that is remote from the aortic valve complex of the subject; and a flexible prosthetic heart valve component, coupled to the support frame, wherein the support frame is shaped so as to define an upstream inlet with respect to blood flow during systole, at least a portion of which extends outside of the delivery tube, wherein the upstream inlet comprises upstream-most portions that are tapered in an upstream direction toward a central longitudinal axis of the prosthesis when the prosthesis assumes the compressed delivery state, and wherein the portion of the upstream inlet has a greatest outer inner diameter that is greater than an outer tube diameter of the delivery tube, when the prosthesis assumes the compressed delivery state when placed partially within the delivery tube, and further comprising an introducer sheath into which the delivery tube and valve prosthesis are placed, the introducer sheath having an inner sheath diameter less than the greatest outer inlet diameter (a) when the prosthesis assumes the compressed delivery state when placed partially within the delivery tube, and (b) before the valve prosthesis is placed into the introducer sheath.

10. The assembly according to claim 9, wherein the inner sheath diameter is no greater than 0.2 mm greater than the delivery tube outer diameter.

11. The assembly according to claim 1, wherein the portion of the inlet has a diameter that first increases along an upstream direction, and subsequently monotonically decreases along the upstream direction, when the prosthesis assumes the compressed delivery state when placed partially within the delivery tube.

12. The assembly according to claim 11, wherein the upstream inlet has upstream-most elements that converge within 2 mm of a central longitudinal axis of the valve prosthesis when the prosthesis assumes the compressed delivery state when placed partially within the delivery tube.

13. The assembly according to claim 11, wherein the prosthesis is shaped so as to define a downstream section, and a throat section between the downstream section and the portion of the inlet, and wherein a diameter of the prosthesis, when it assumes the compressed delivery state when placed partially within the delivery tube, decreases in the upstream direction from the downstream section to the throat section, and increases in the upstream direction from the throat section to the portion of the inlet.

14. The assembly according to claim 1, wherein the upstream inlet has upstream-most elements, and wherein the apparatus further comprises:

a neutral tube that is concentric with the delivery tube, wherein the valve prosthesis is partially held between the delivery tube and the neutral tube when the valve prosthesis assumes the compressed delivery state when partially placed in the delivery tube; and a delivery tip, which is removably coupled to the neutral tube, and not coupled to the delivery tube, such that the upstream-most elements of the inlet rest against a downstream side of the delivery tip when the prosthesis assumes the collapsed delivery state.

15. The assembly according to claim 14, wherein the delivery tip has a length of less than 10 mm, and a maximum diameter of less than 4 mm.

16. The assembly according to claim 1, wherein when the prosthesis assumes the uncompressed implantation state, the support frame is shaped so as to define two curved portions connected by an intermediary portion, shaped such that when the intermediary portion is subjected to an upstream axial force applied by the delivery tube when the prosthesis is placed partially within the delivery tube, resulting vector component forces compress the upstream inlet toward the central longitudinal axis.

\* \* \* \* \*